(12) United States Patent
Domke et al.

(10) Patent No.: US 9,036,892 B2
(45) Date of Patent: May 19, 2015

(54) SYSTEMS AND METHODS FOR DATA ENTRY IN A NON-DESTRUCTIVE TESTING SYSTEM

(71) Applicant: General Electric Company, Schenectady, NY (US)

(72) Inventors: Michael Christopher Domke, Skaneateles, NY (US); Thomas Eldred Lambdin, Auburn, NY (US); Jason Howard Messinger, Andover, MA (US); Charles Burton Theurer, Alplaus, NY (US)

(73) Assignee: General Electric Company, Schenectady, NY (US)

( * ) Notice: Subject to any disclaimer, the term of this patent is extended or adjusted under 35 U.S.C. 154(b) by 147 days.

(21) Appl. No.: 13/732,327

(22) Filed: Dec. 31, 2012

(65) Prior Publication Data

US 2014/0185913 A1    Jul. 3, 2014

(51) Int. Cl.
| | | |
|---|---|---|
| G06K 9/00 | (2006.01) | |
| G06T 7/00 | (2006.01) | |
| G01N 27/60 | (2006.01) | |
| G01N 29/44 | (2006.01) | |
| G01N 23/04 | (2006.01) | |
| G01N 27/90 | (2006.01) | |

(52) U.S. Cl.
CPC .............. *G06T 7/0004* (2013.01); *G01N 27/60* (2013.01); *G01N 29/44* (2013.01); *G01N 23/04* (2013.01); *G01N 27/90* (2013.01)

(58) Field of Classification Search
CPC ...................................................... G06T 7/0004
USPC .......................................................... 382/141
See application file for complete search history.

(56) References Cited

U.S. PATENT DOCUMENTS

| | | |
|---|---|---|
| 4,701,892 A | 10/1987 | Anderson |
| 5,763,786 A | 6/1998 | Camplin et al. |
| 6,317,039 B1 | 11/2001 | Thomason |
| 6,830,545 B2 | 12/2004 | Bendall |
| 7,313,759 B2 * | 12/2007 | Sinisi ............................ 715/203 |
| 8,033,426 B2 * | 10/2011 | Becker et al. ................... 222/52 |
| 8,059,882 B2 | 11/2011 | Amidi |
| 8,108,168 B2 | 1/2012 | Sharp et al. |

(Continued)

FOREIGN PATENT DOCUMENTS

| | | |
|---|---|---|
| GB | 2473230 A | 3/2011 |
| WO | 9917102 A1 | 4/1999 |

(Continued)

OTHER PUBLICATIONS

Sorrel, Charlie. iControlPad Ships at Last [online], [retrieved on Mar. 21, 2013]. Retrieved from the Internet <URL: http://www.wired.com/gadgetlab/2011/11/icontrolpad-ships-at-last/>.

(Continued)

*Primary Examiner* — Utpal Shah
(74) *Attorney, Agent, or Firm* — Fletcher Yoder P.C.

(57) ABSTRACT

Systems and methods for entering data acquired from a non-destructive testing (NDT) system may include obtaining information related to an inspection using a non-destructive testing (NDT) inspection device. After obtaining the information, the method may include generating an inspection template, a report, metadata, or any combination thereof based on the information related to the inspection.

16 Claims, 11 Drawing Sheets

(56) References Cited

U.S. PATENT DOCUMENTS

| | | | |
|---|---|---|---|
| 8,255,170 B2* | 8/2012 | Kollgaard et al. | 702/34 |
| 8,413,039 B2* | 4/2013 | Casey | 715/203 |
| 8,739,059 B2* | 5/2014 | Rabenold et al. | 715/780 |
| 2002/0198997 A1 | 12/2002 | Linthicum et al. | |
| 2005/0228688 A1* | 10/2005 | Visser et al. | 705/1 |
| 2007/0194115 A1 | 8/2007 | Logan et al. | |
| 2007/0266782 A1* | 11/2007 | Bartz et al. | 73/156 |
| 2008/0006087 A1 | 1/2008 | Winter et al. | |
| 2008/0108261 A1* | 5/2008 | Swan et al. | 441/89 |
| 2008/0147347 A1* | 6/2008 | Shaw et al. | 702/108 |
| 2009/0192763 A1* | 7/2009 | Gardner et al. | 702/187 |
| 2010/0313664 A1 | 12/2010 | Cain | |
| 2011/0054806 A1* | 3/2011 | Goldfine et al. | 702/34 |
| 2011/0320959 A1* | 12/2011 | Maly | 715/752 |
| 2013/0151428 A1* | 6/2013 | Hesse et al. | 705/318 |
| 2013/0219295 A1* | 8/2013 | Feldman et al. | 715/751 |
| 2014/0067188 A1* | 3/2014 | Mian | 701/28 |
| 2014/0114612 A1* | 4/2014 | Yoskovitz et al. | 702/184 |

FOREIGN PATENT DOCUMENTS

| | | | |
|---|---|---|---|
| WO | 2008074917 A1 | 6/2008 | |
| WO | 2009083674 A1 | 7/2009 | |

OTHER PUBLICATIONS

OmniScan MX [online]. p. 5. Olympus, 2010 [retrieved on Mar. 28, 2013]. Retrieved from the Internet: <URL: www.olympus-ims.com/en/omniscan-mx/>.

Georgeson, Gary. [online], [retrieved on Mar. 28, 2013]. http://www.meetingdata.utcdayton.com/agenda/airworthiness/2012/proceedings/presentations/P5526.pdf.

Phasor XS User's Manual [online]. General Electric: Measurement & Control Solutions. [retrieved on Mar. 28, 2013]. Retrieved from the Internet: <URL: www.ge-mcs.com/download/ultrasound/portable-flaw-detectors/Phasor%20Series/om-phasor-en_rev10.pdf>, 2010.

USM Vision 1.2—A Total Weld Inspection Solution to Increase Productivity in New Process Pipework Fabrication [online]. General Electric: Measurement & Control. [retrieved on Mar. 28, 2013]. Retrieved from the Internet: <URL: www.ge-mcs.com/download/ultrasound/portable-flaw-detectors/usm-vision/GEIT-USMVision-20058EN_LR.pdf>, 2012.

PCT Invitation to Pay Additional Fees issued Mar. 31, 2014 in connection with corresponding PCT Patent Application No. PCT/US2013/072545.

U.S. Appl. No. 13/732,238, filed Dec. 31, 2012, Michael Christopher Domke.

U.S. Appl. No. 13/732,252, filed Dec. 31, 2012, Kevin Andrew Coombs.

U.S. Appl. No. 13/732,261, filed Dec. 31, 2012, Eugene Schiefer.

U.S. Appl. No. 13/732,281, filed Dec. 31, 2012, Jason Howard Messinger.

U.S. Appl. No. 13/732,293, filed Dec. 31, 2012, Jason Howard Messinger.

U.S. Appl. No. 13/732,303, filed Dec. 31, 2012, Thomas Eldred Lambdin.

U.S. Appl. No. 13/732,268, filed Dec. 31, 2012, Scott Leo Sbihli.

U.S. Appl. No. 13/732,309, filed Dec. 31, 2012, Jason Howard Messinger.

U.S. Appl. No. 13/732,272, filed Dec. 31, 2012, Jason Howard Messinger.

U.S. Appl. No. 13/732,319, filed Dec. 31, 2012, Michael Christopher Domke.

U.S. Appl. No. 13/747,408, filed Jan. 22, 2013, Michael Christopher Domke.

U.S. Appl. No. 13/747,435, filed Jan. 22, 2013, Jason Howard Messinger.

U.S. Appl. No. 13/747,438, filed Jan. 22, 2013, Jason Howard Messinger.

U.S. Appl. No. 13/747,457, filed Jan. 22, 2013, Jason Howard Messinger.

U.S. Appl. No. 13/747,453, filed Jan. 22, 2013, Sekhar Soorianarayanan.

U.S. Appl. No. 13/747,429, filed Jan. 22, 2013, Sekhar Soorianarayanan.

U.S. Appl. No. 13/747,464, filed Jan. 22, 2013, Sekhar Soorianarayanan.

U.S. Appl. No. 13/747,443, filed Jan. 22, 2013, Jason Howard Messinger.

U.S. Appl. No. 13/747,449, filed Jan. 22, 2013, Michael Christopher Domke.

U.S. Appl. No. 13/747,456, filed Jan. 22, 2013, Michael Christopher Domke.

U.S. Appl. No. 13/747,416, filed Jan. 22, 2013, Michael Christopher Domke.

U.S. Appl. No. 13/800,015, filed Mar. 13, 2013, Kevin Andrew Coombs.

PCT Search Report and Written opinion issued in connection with corresponding Application No. PCT/US2013/072545 on Jul. 23, 2014.

* cited by examiner

SYSTEMS AND METHODS FOR DATA ENTRY IN A NON-DESTRUCTIVE TESTING SYSTEM

BACKGROUND

The subject matter disclosed herein relates to configuration of inspection instruments. More specifically, the subject matter disclosed herein relates to automatically configuring inspection equipment based at least partially upon identification of the object being inspected.

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support. During equipment operations, the equipment may degrade, encounter undesired conditions such as corrosion, wear and tear, and so on, potentially affecting overall equipment effectiveness. Certain inspection techniques, such as non-destructive inspection techniques or non-destructive testing (NDT) techniques, may be used to detect undesired equipment conditions.

NDT relates to the examination of an object, material, or system without reducing future usefulness. In particular NDT inspections may be used to determine the integrity of a product using time-sensitive inspection data relating to a particular product. For example, NDT inspections may observe the "wear and tear" of a product over a particular time-period.

Many forms of NDT are currently known. For example, perhaps the most common NDT method is visual examination. During a visual examination, an inspector may, for example, simply visually inspect an object for visible imperfections. Alternatively, visual inspections may be conducted using optical technologies such as a computer-guided camera, a borescope, etc. Radiography is another form of NDT. Radiography relates to using radiation (e.g., x-rays and/or gamma rays) to detect thickness and/or density changes to a product, which may denote a defect in the product. Further, ultrasonic testing relates to transmitting high-frequency sound waves into a product to detect changes and/or imperfections to the product. Using a pulse-echo technique, sound it introduced into the product and echoes from the imperfections are returned to a receiver, signaling that the imperfection exists. Many other forms of NDT exist. For example, magnetic particle testing, penetrant testing, electromagnetic testing, leak testing, and acoustic emission testing, to name a few.

Oftentimes, product inspections may be quite complex due to the complex nature of the product being tested. For example, airplanes are very complex machines where safety and inspection standards are of the utmost importance. The Boeing 777 aircraft may have as many 3 million parts. Accordingly, a tremendous amount of time and effort is used to inspect these aircraft on a periodic basis. As may be appreciated, massive amounts of data may be gathered and used in the inspection process.

Unfortunately, in conventional inspection systems, data is manually entered into inspection reports and the like. These manual entries may lead to inefficient use of inspection personnel. Accordingly, improved systems and methods for entering data related to an inspection process for an inspection report or the like are desired.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a method for entering data acquired from a non-destructive testing (NDT) system may first include obtaining information related to an inspection using a non-destructive testing (NDT) inspection device. After obtaining the information, the method may include generating an inspection template, a report, metadata, or any combination thereof based on the information related to the inspection.

In another embodiment, a system may include a non-destructive testing (NDT) inspection device. The NDT inspection device may include an input device that may obtain information regarding an inspection. The NDT inspection device may also include a processor that may receive, via the input device, the information. After receiving the information, the processor may enter the information into an inspection report associated with the inspection.

In yet another embodiment, a tangible, non-transitory, computer readable medium may include computer readable instructions that may receive an image that corresponds to an inspection report. The computer readable instructions may also receive, via a non-destructive testing (NDT) inspection device, information relating to an inspection. After receiving the information, the computer readable instructions may include generating a report template based on the inspection report and the information.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
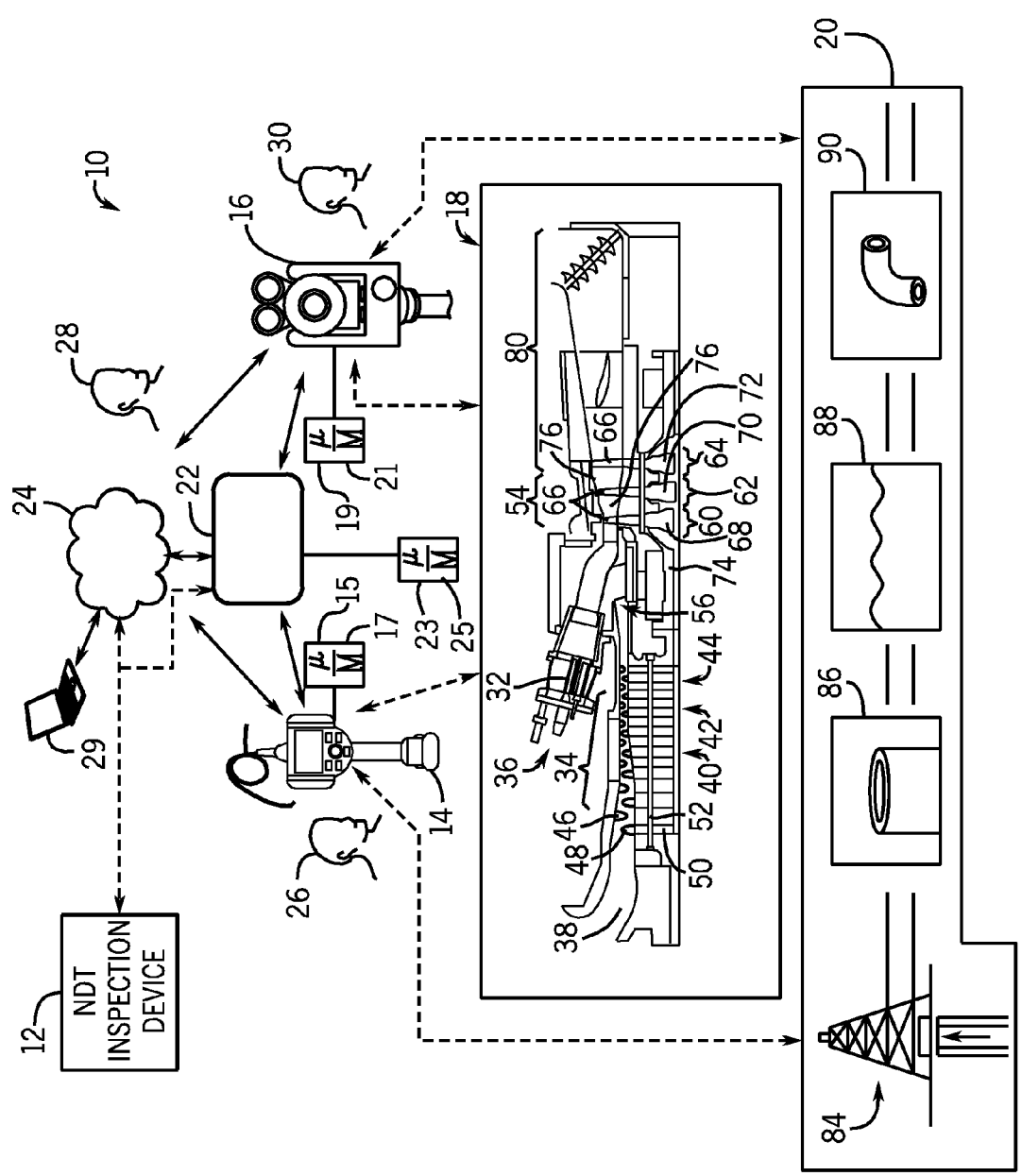
FIG. 1 is a block diagram illustrating an embodiment of a distributed non-destructive testing (NDT) system, including a mobile device.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of inspection and testing techniques, including non-destructive testing (NDT) or inspection systems. In the NDT system, certain techniques such as borescopic inspection, weld inspection, remote visual inspections, x-ray inspection, ultrasonic inspection, eddy current inspection, and the like, may be used to analyze and detect a variety of conditions, including but not limited to corrosion, equipment wear and tear, cracking, leaks, and so on. The techniques described herein provide for improved NDT systems suitable for borescopic inspection, remote visual inspections, x-ray inspection, ultrasonic inspection, and/or eddy current inspection, enabling enhanced data gathering, data analysis, inspection/testing processes, and NDT collaboration techniques.

The improved NDT systems described herein may include inspection equipment using wireless conduits suitable for communicatively coupling the inspection equipment to mobile devices, such as tablets, smart phones, and augmented reality eyeglasses; to computing devices, such as notebooks, laptops, workstations, personal computers; and to "cloud" computing systems, such as cloud-based NDT ecosystems, cloud analytics, cloud-based collaboration and workflow systems, distributed computing systems, expert systems and/or knowledge-based systems. Indeed, the techniques described herein may provide for enhanced NDT data gathering, analysis, and data distribution, thus improving the detection of undesired conditions, enhancing maintenance activities, and increasing returns on investment (ROI) of facilities and equipment.

In one embodiment, a tablet may be communicatively coupled to the NDT inspection device (e.g., borescope, transportable pan-tilt-zoom camera, eddy current device, x-ray inspection device, ultrasonic inspection device), such as a MENTOR™ NDT inspection device, available from General Electric, Co., of Schenectady, N.Y., and used to provide, for example, enhanced wireless display capabilities, remote control, data analytics and/or data communications to the NDT inspection device. While other mobile devices may be used, the use of the tablet is apt, however, insofar as the tablet may provide for a larger, higher resolution display, more powerful processing cores, an increased memory, and improved battery life. Accordingly, the tablet may address certain issues, such as providing for improved visualization of data, improving the manipulatory control of the inspection device, and extending collaborative sharing to a plurality of external systems and entities.

Keeping the foregoing in mind, the present disclosure is directed towards sharing data acquired from the NDT system and/or control of applications and/or devices in the NDT system. Generally, data generated from the NDT system may be automatically distributed to various people or groups of people using techniques disclosed herein. Moreover, content displayed by an application used to monitor and/or control devices in the NDT system may be shared between individuals to create a virtual collaborative environment for monitoring and controlling the devices in the NDT system.

By way of introduction, and turning now to FIG. 1, the figure is a block diagram of an embodiment of distributed NDT system 10. In the depicted embodiment, the distributed NDT system 10 may include one or more NDT inspection devices 12. The NDT inspection devices 12 may be divided into at least two categories. In one category, depicted in FIG. 1, the NDT inspection devices 12 may include devices suitable for visually inspecting a variety of equipment and environments. In another category, described in more detail with respect to FIG. 2 below, the NDT devices 12 may include devices providing for alternatives to visual inspection modalities, such as x-ray inspection modalities, eddy current inspection modalities, and/or ultrasonic inspection modalities.

In the depicted first example category of FIG. 1, the NDT inspection devices 12 may include a borescope 14 having one or more processors 15 and a memory 17, and a transportable pan-tilt-zoom (PTZ) camera 16 having one or more processors 19 and a memory 21. In this first category of visual inspection devices, the bore scope 14 and PTZ camera 16 may be used to inspect, for example, a turbo machinery 18, and a facility or site 20. As illustrated, the bore scope 14 and the PTZ camera 16 may be communicatively coupled to a mobile device 22 also having one or more processors 23 and a memory 25. The mobile device 22 may include, for example, a tablet, a cell phone (e.g., smart phone), a notebook, a laptop, or any other mobile computing device. The use of a tablet, however, is apt insofar as the tablet provides for a good balance between screen size, weight, computing power, and battery life. Accordingly, in one embodiment, the mobile device 22 may be the tablet mentioned above, that provides for touchscreen input. The mobile device 22 may be communicatively coupled to the NDT inspection devices 12, such as the bore scope 14 and/or the PTZ camera 16, through a variety of wireless or wired conduits. For example, the wireless conduits may include WiFi (e.g., Institute of Electrical and Electronics Engineers [IEEE] 802.11X), cellular conduits (e.g., high speed packet access [HSPA], HSPA+, long term evolution [LTE], WiMax), near field communications (NFC), Bluetooth, personal area networks (PANs), and the like. The wireless conduits may use a variety of communication protocols, such as TCP/IP, UDP, SCTP, socket layers, and so on. In certain embodiments, the wireless or wired conduits may include secure layers, such as secure socket layers (SSL), virtual private network (VPN) layers, encrypted layers, challenge key authentication layers, token authentication layers, and so on. Wired conduits may include proprietary cabling, RJ45 cabling, co-axial cables, fiber optic cables, and so on.

Additionally or alternatively, the mobile device 22 may be communicatively coupled to the NDT inspection devices 12, such as the borescope 14 and/or the PTZ camera 16, through the "cloud" 24. Indeed, the mobile device 22 may use the cloud 24 computing and communications techniques (e.g., cloud-computing network), including but not limited to HTTP, HTTPS, TCP/IP, service oriented architecture (SOA) protocols (e.g., simple object access protocol [SOAP], web services description languages (WSDLs)) to interface with the NDT inspection devices 12 from any geographic location, including geographic locations remote from the physical location about to undergo inspection. Further, in one embodiment, the mobile device 22 may provide "hot spot" functionality in which mobile device 22 may provide wireless access point (WAP) functionality suitable for connecting the NDT inspection devices 12 to other systems in the cloud 24, or connected to the cloud 24, such as a computing system 29 (e.g., computer, laptop, virtual machine(s) [VM], desktop, workstation). Accordingly, collaboration may be enhanced by providing for multi-party workflows, data gathering, and data analysis.

For example, a borescope operator 26 may physically manipulate the borescope 14 at one location, while a mobile device operator 28 may use the mobile device 22 to interface with and physically manipulate the bore scope 14 at a second location through remote control techniques. The second location may be proximate to the first location, or geographically distant from the first location. Likewise, a camera operator 30 may physically operate the PTZ camera 16 at a third location, and the mobile device operator 28 may remote control PTZ camera 16 at a fourth location by using the mobile device 22. The fourth location may be proximate to the third location, or geographically distant from the third location. Any and all control actions performed by the operators 26 and 30 may be additionally performed by the operator 28 through the mobile device 22. Additionally, the operator 28 may communicate with the operators 26 and/or 30 by using the devices 14, 16, and 22 through techniques such as voice over IP (VOIP), virtual whiteboarding, text messages, and the like. By providing for remote collaboration techniques between the operator 28 operator 26, and operator 30, the techniques described herein may provide for enhanced workflows and increase resource efficiencies. Indeed, nondestructive testing processes may leverage the communicative coupling of the cloud 24 with the mobile device 22, the NDT inspection devices 12, and external systems coupled to the cloud 24.

In one mode of operation, the mobile device 22 may be operated by the bore scope operator 26 and/or the camera operator 30 to leverage, for example, a larger screen display, more powerful data processing, as well as a variety of interface techniques provided by the mobile device 22, as described in more detail below. Indeed, the mobile device 22 may be operated alongside or in tandem with the devices 14 and 16 by the respective operators 26 and 30. This enhanced flexibility provides for better utilization of resources, including human resources, and improved inspection results.

Whether controlled by the operator 28, 26, and/or 30, the borescope 14 and/or PTZ camera 16 may be used to visually inspect a wide variety of equipment and facilities. For example, the bore scope 14 may be inserted into a plurality of borescope ports and other locations of the turbomachinery 18, to provide for illumination and visual observations of a number of components of the turbomachinery 18. In the depicted embodiment, the turbo machinery 18 is illustrated as a gas turbine suitable for converting carbonaceous fuel into mechanical power. However, other equipment types may be inspected, including compressors, pumps, turbo expanders, wind turbines, hydroturbines, industrial equipment, and/or residential equipment. The turbomachinery 18 (e.g., gas turbine) may include a variety of components that may be inspected by the NDT inspection devices 12 described herein.

With the foregoing in mind, it may be beneficial to discuss certain turbomachinery 18 components that may be inspected by using the embodiments disclosed herein. For example, certain components of the turbomachinery 18 depicted in FIG. 1, may be inspected for corrosion, erosion, cracking, leaks, weld inspection, and so on. Mechanical systems, such as the turbomachinery 18, experience mechanical and thermal stresses during operating conditions, which may require periodic inspection of certain components. During operations of the turbomachinery 18, a fuel such as natural gas or syngas, may be routed to the turbomachinery 18 through one or more fuel nozzles 32 into a combustor 36. Air may enter the turbomachinery 18 through an air intake section 38 and may be compressed by a compressor 34. The compressor 34 may include a series of stages 40, 42, and 44 that compress the air. Each stage may include one or more sets of stationary vanes 46 and blades 48 that rotate to progressively increase the pressure to provide compressed air. The blades 48 may be attached to rotating wheels 50 connected to a shaft 52. The compressed discharge air from the compressor 34 may exit the compressor 34 through a diffuser section 56 and may be directed into the combustor 36 to mix with the fuel. For example, the fuel nozzles 32 may inject a fuel-air mixture into the combustor 36 in a suitable ratio for optimal combustion, emissions, fuel consumption, and power output. In certain embodiments, the turbomachinery 18 may include multiple combustors 36 disposed in an annular arrangement. Each combustor 36 may direct hot combustion gases into a turbine 54.

As depicted, the turbine 54 includes three separate stages 60, 62, and 64 surrounded by a casing 76. Each stage 60, 62, and 64 includes a set of blades or buckets 66 coupled to a respective rotor wheel 68, 70, and 72, which are attached to a shaft 74. As the hot combustion gases cause rotation of turbine blades 66, the shaft 74 rotates to drive the compressor 34 and any other suitable load, such as an electrical generator. Eventually, the turbomachinery 18 diffuses and exhausts the combustion gases through an exhaust section 80. Turbine components, such as the nozzles 32, intake 38, compressor 34, vanes 46, blades 48, wheels 50, shaft 52, diffuser 56, stages 60, 62, and 64, blades 66, shaft 74, casing 76, and exhaust 80, may use the disclosed embodiments, such as the NDT inspection devices 12, to inspect and maintain said components.

Additionally, or alternatively, the PTZ camera 16 may be disposed at various locations around or inside of the turbo machinery 18, and used to procure visual observations of these locations. The PTZ camera 16 may additionally include one or more lights suitable for illuminating desired locations, and may further include zoom, pan and tilt techniques described in more detail below with respect to FIG. 4, useful for deriving observations around in a variety of difficult to reach areas. The borescope 14 and/or the camera 16 may be additionally used to inspect the facilities 20, such as an oil and gas facility 20. Various equipment such as oil and gas equipment 84, may be inspected visually by using the borescope 14 and/or the PTZ camera 16. Advantageously, locations such as the interior of pipes or conduits 86, underwater (or underfluid) locations 88, and difficult to observe locations such as locations having curves or bends 90, may be visually inspected by using the mobile device 22 through the borescope 14 and/or PTZ camera 16. Accordingly, the mobile device operator 28 may more safely and efficiently inspect the equipment 18, 84 and locations 86, 88, and 90, and share observations in real-time or near real-time with location geographically distant from the inspection areas. It is to be understood that other NDT inspection devices 12 may be use the embodiments described herein, such as fiberscopes (e.g., articulating fiberscope, non-articulating fiberscope), and remotely operated vehicles (ROVs), including robotic pipe inspectors and robotic crawlers.

Figure 2:
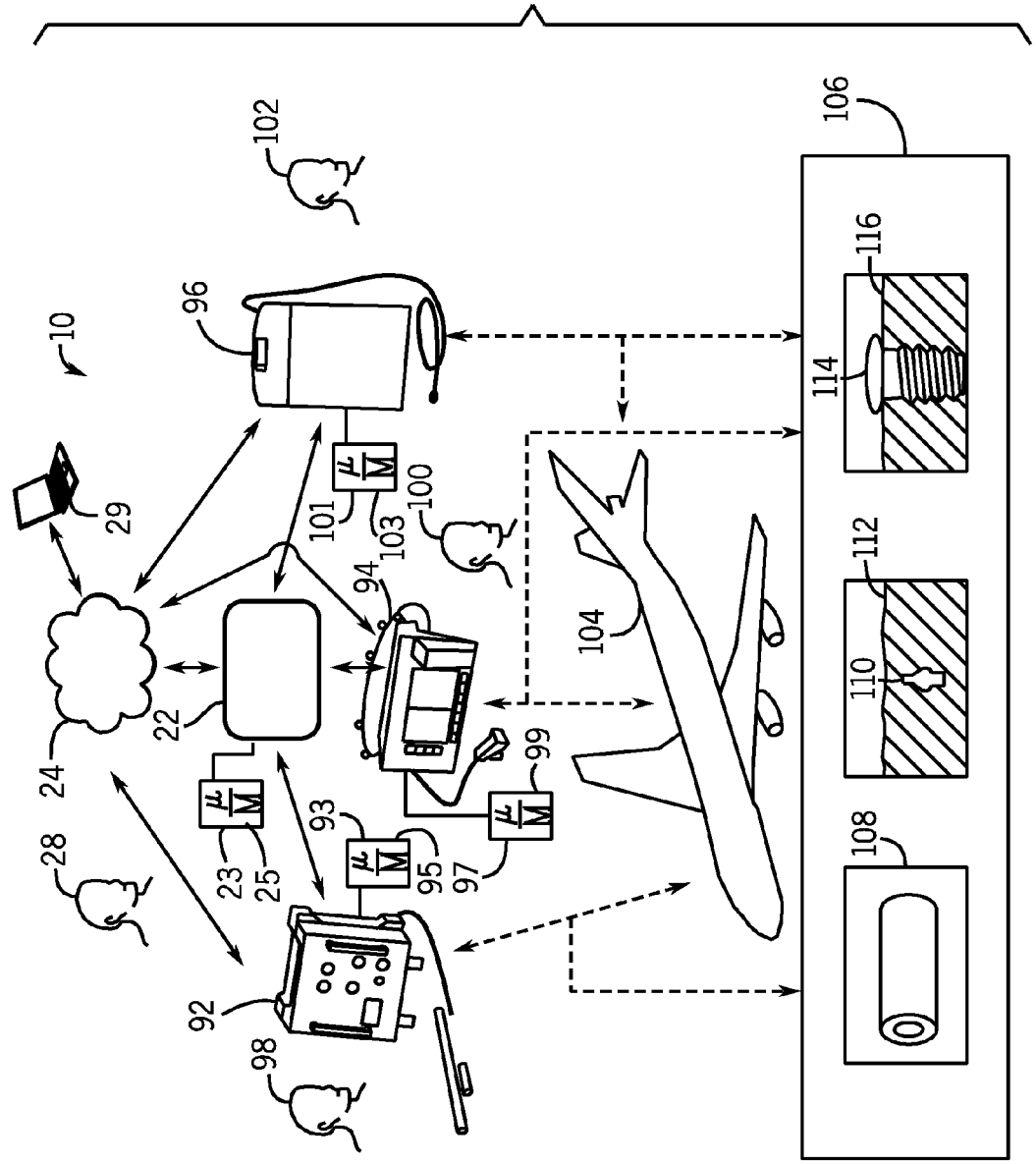
FIG. 2 is a block diagram illustrating further details of an embodiment of the distributed NDT system of FIG. 1.

Turning now to FIG. 2, the figure is a block diagram of an embodiment of the distributed NDT system 10 depicting the second category of NDT inspection devices 12 that may be able to provide for alternative inspection data to visual inspection data. For example, the second category of NDT inspection devices 12 may include an eddy current inspection device 92, an ultrasonic inspection device, such as an ultrasonic flaw detector 94, and an x-ray inspection device, such a digital radiography device 96. The eddy current inspection device 92 may include one or more processors 93 and a memory 95. Likewise, the ultrasonic flaw detector 94 may include one or more processors 97 and a memory 104. Similarly, the digital radiography device 96 may include one or more processors 101 and a memory 103. In operations, the eddy current inspection device 92 may be operated by an eddy current operator 98, the ultrasonic flaw detector 94 may be operated by an ultrasonic device operator 100, and the digital radiography device 96 may be operated by a radiography operator 102.

As depicted, the eddy current inspection device 92, the ultrasonic flaw detector 94, and the digital radiography inspection device 96, may be communicatively coupled to the mobile device 22 by using wired or wireless conduits, including the conduits mentioned above with respect to FIG. 1. Additionally, or alternatively, the devices 92, 94, and 96 may be coupled to the mobile device 22 by using the cloud 24, for example the borescope 14 may be connected to a cellular "hotspot," and use the hotspot to connect to one or more experts in borescopic inspection and analsysis. Accordingly, the mobile device operator 28 may remotely control various aspects of operations of the devices 92, 94, and 96 by using the mobile device 22, and may collaborate with the operators 98, 100, and 102 through voice (e.g., voice over IP [VOIP]), data sharing (e.g., whiteboarding), providing data analytics, expert support and the like, as described in more detail herein.

Accordingly, it may be possible to enhance the visual observation of various equipment, such as an aircraft system 104 and facilities 106, with x-ray observation modalities, ultrasonic observation modalities, and/or eddy current observation modalities. For example, the interior and the walls of pipes 108 may be inspected for corrosion and/or erosion. Likewise, obstructions or undesired growth inside of the pipes 108 may be detected by using the devices 92, 94, and/or 96. Similarly, fissures or cracks 110 disposed inside of certain ferrous or non-ferrous material 112 may be observed. Additionally, the disposition and viability of parts 114 inserted inside of a component 116 may be verified. Indeed, by using the techniques described herein, improved inspection of equipment and components 104, 108, 112 and 116 may be provided. For example, the mobile device 22 may be used to interface with and provide remote control of the devices 14, 16, 92, 94, and 96.

Figure 3:
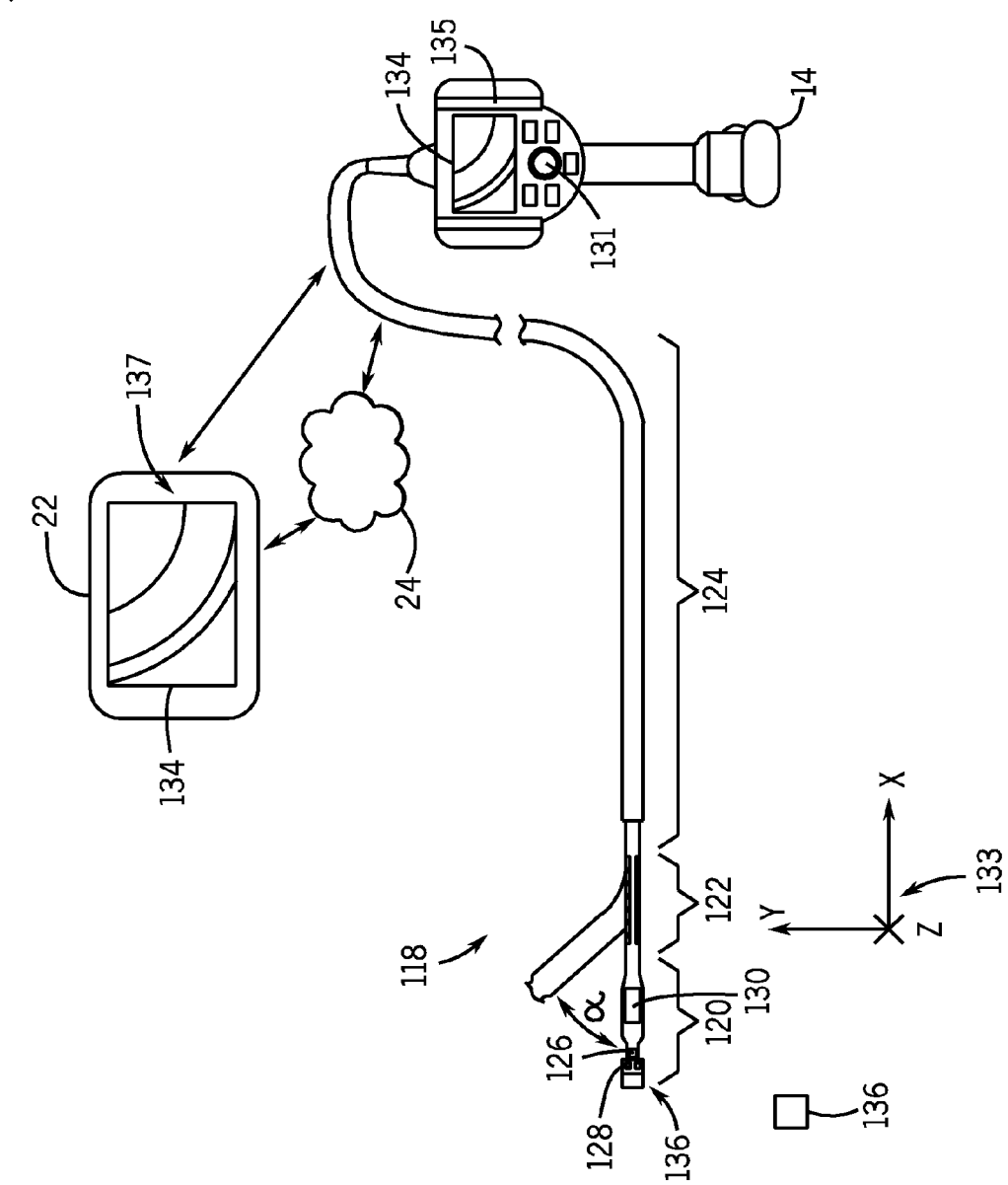
FIG. 3 is a front view illustrating an embodiment of a borescope system 14 communicatively coupled to the mobile device of FIG. 1 and a "cloud;"

FIG. 3 is a front view of the borescope 14 coupled to the mobile device 22 and the cloud 24. Accordingly, the boresecope 14 may provide data to any number of devices connected to the cloud 24 or inside the cloud 24. As mentioned above, the mobile device 22 may be used to receive data from the borescope 14, to remote control the borescope 14, or a combination thereof. Indeed, the techniques described herein enable, for example, the communication of a variety of data from the borescope 14 to the mobile device 22, including but not limited to images, video, and sensor measurements, such as temperature, pressure, flow, clearance (e.g., measurement between a stationary component and a rotary component), and distance measurements. Likewise, the mobile device 22 may communicate control instructions, reprogramming instructions, configuration instructions, and the like, as described in more detail below.

As depicted the borescope 14, includes an insertion tube 118 suitable for insertion into a variety of location, such as inside of the turbomachinery 18, equipment 84, pipes or conduits 86, underwater locations 88, curves or bends 90, varies locations inside or outside of the aircraft system 104, the interior of pipe 108, and so on. The insertion tube 118 may include a head end section 120, an articulating section 122, and a conduit section 124. In the depicted embodiment, the head end section 120 may include a camera 126, one or more lights 128 (e.g., LEDs), and sensors 130. As mentioned above, the borescope's camera 126 may provide images and video suitable for inspection. The lights 128 may be used to provide for illumination when the head end 120 is disposed in locations having low light or no light.

During use, the articulating section 122 may be controlled, for example, by the mobile device 22 and/or a physical joy stick 131 disposed on the borescope 14. The articulating sections 122 may steer or "bend" in various dimensions. For example, the articulation section 122 may enable movement of the head end 120 in an X-Y plane X-Z plane and/or Y-Z plane of the depicted XYZ axes 133. Indeed, the physical joystick 131 and/or the mobile device 22 may both be used alone or in combination, to provide control actions suitable for disposing the head end 120 at a variety of angles, such as the depicted angle α. In this manner, the borescope head end 120 may be positioned to visually inspect desired locations. The camera 126 may then capture, for example, a video 134, which may be displayed in a screen 135 of the borescope 14 and a screen 137 of the mobile device 22, and may be recorded by the borescope 14 and/or the mobile device 22. In one embodiment, the screens 135 and 137 may be multi-touchscreens using capacitance techniques, resistive techniques, infrared grid techniques, and the like, to detect the touch of a stylus and/or one or more human fingers. Additionally or alternatively, images and the video 134 may be transmitted into the cloud 24.

Other data, including but not limited to sensor 130 data, may additionally be communicated and/or recorded by the borescope 14. The sensor 130 data may include temperature data, distance data, clearance data (e.g., distance between a rotating and a stationary component), flow data, and so on. In certain embodiments, the borescope 14 may include a plurality of replacement tips 136. For example, the replacement tips 136 may include retrieval tips such as snares, magnetic tips, gripper tips, and the like. The replacement tips 136 may additionally include cleaning and obstruction removal tools, such as wire brushes, wire cutters, and the like. The tips 136 may additionally include tips having differing optical characteristics, such as focal length, stereoscopic views, 3-dimensional (3D) phase views, shadow views, and so on. Additionally or alternatively, the head end 120 may include a removable and replaceable head end 120. Accordingly, a plurality of head ends 120 may be provided at a variety of diameters, and the insertion tube 118 may be disposed in a number of locations having openings from approximately one millimeter to ten millimeters or more. Indeed, a wide variety of equipment and facilities may be inspected, and the data may be shared through the mobile device 22 and/or the cloud 24.

Figure 4:
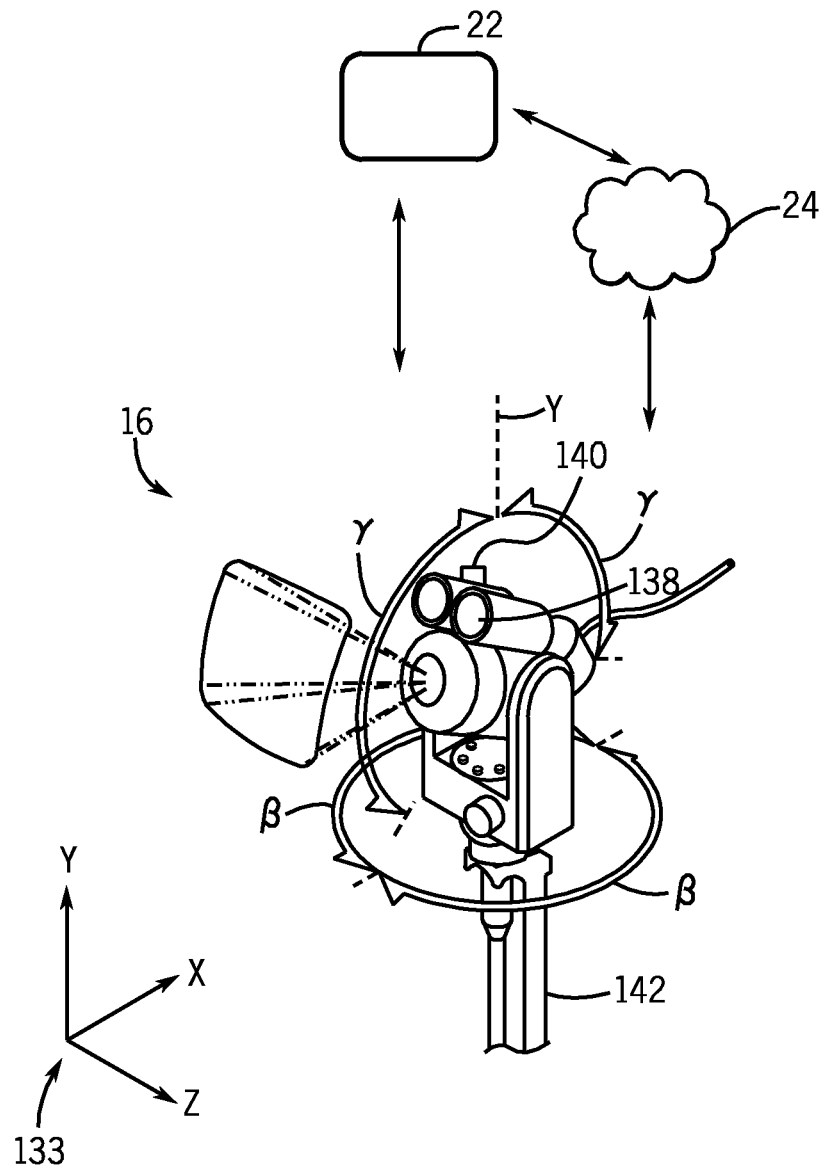
FIG. 4 is an illustration of an embodiment of a pan-tilt-zoom (PTZ) camera system communicatively coupled to the mobile device of FIG. 1.

FIG. 4 is a perspective view of an embodiment of the transportable PTZ camera 16 communicatively coupled to the mobile device 22 and to the cloud 24. As mentioned above, the mobile device 22 and/or the cloud 24 may remotely manipulate the PTZ camera 16 to position the PTZ camera 16 to view desired equipment and locations. In the depicted example, the PTZ camera 16 may be tilted and rotated about the Y-axis. For example, the PTZ camera 16 may be rotated at an angle β between approximately 0° to 180°, 0° to 270°, 0° to 360°, or more about the Y-axis. Likewise, the PTZ camera 16 may be tilted, for example, about the Y-X plane at an angle γ of approximately 0° to 100°, 0° to 120°, 0° to 150°, or more with respect to the Y-Axis. Lights 138 may be similarly controlled, for example, to active or deactivate, and to increase or decrease a level of illumination (e.g., lux) to a desired value. Sensors 140, such as a laser rangefinder, may also be mounted onto the PTZ camera 16, suitable for measuring distance to certain objects. Other sensors 140 may be used, including long-range temperature sensors (e.g., infrared temperature sensors), pressure sensors, flow sensors, clearance sensors, and so on.

The PTZ camera 16 may be transported to a desired location, for example, by using a shaft 142. The shaft 142 enables the camera operator 30 to move the camera and to position the camera, for example, inside of locations 86, 108, underwater 88, into hazardous (e.g., hazmat) locations, and so on. Additionally, the shaft 142 may be used to more permanently secure the PTZ camera 16 by mounting the shaft 142 onto a permanent or semi-permanent mount. In this manner, the PTZ camera 16 may be transported and/or secured at a desired location. The PTZ camera 16 may then transmit, for example by using wireless techniques, image data, video data, sensor 140 data, and the like, to the mobile device 22 and/or cloud 24. Accordingly, data received from the PTZ camera 16 may be remotely analyzed and used to determine the condition and suitability of operations for desired equipment and facilities. Indeed, the techniques described herein may provide for a comprehensive inspection and maintenance process suitable for planning, inspecting, analyzing, and/or sharing a variety of data by using the aforementioned devices 12, 14, 16, 22, 92, 94, 96, and the cloud 24, as described in more detail below with respect to FIG. 5.

Figure 5:
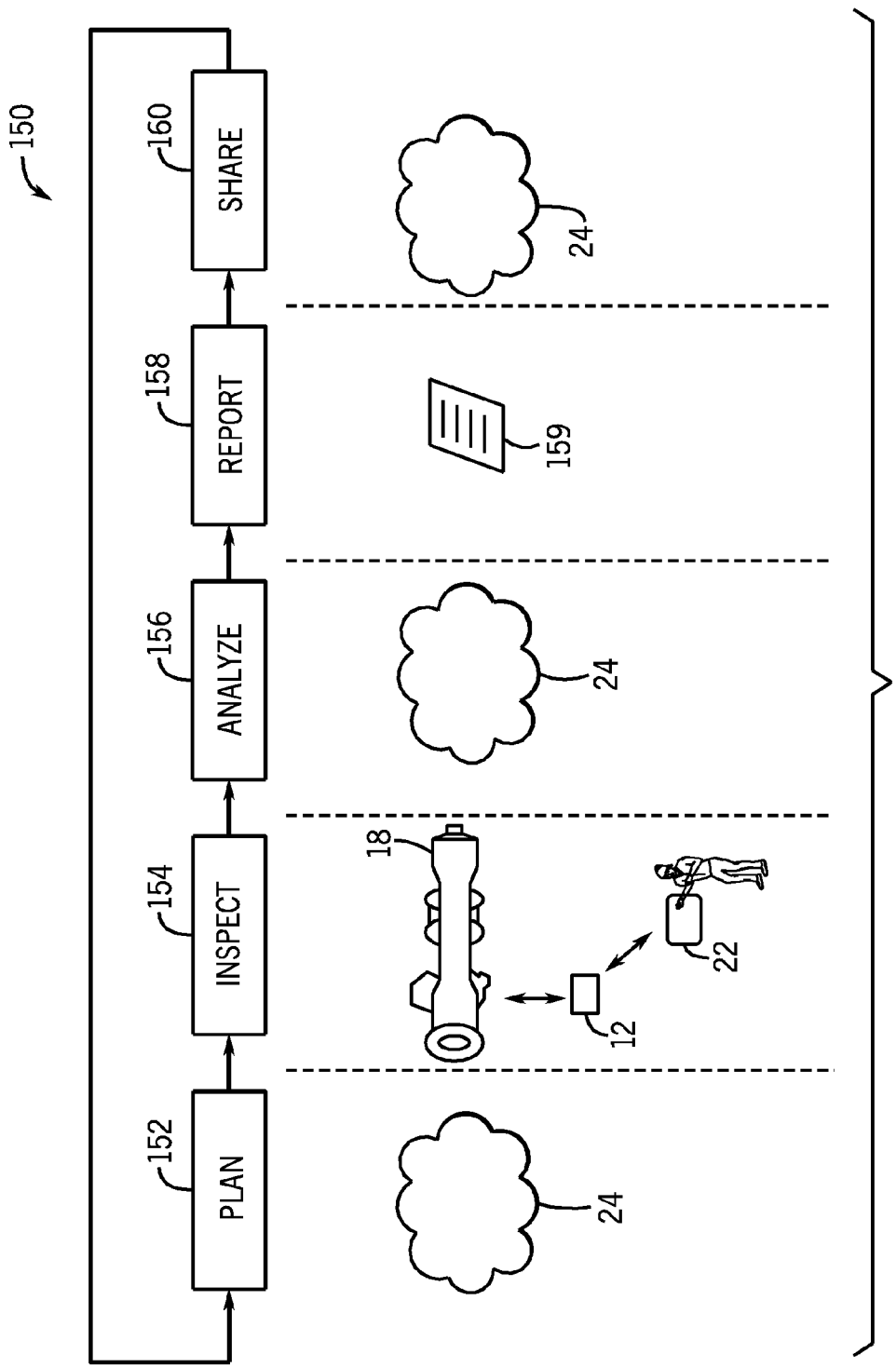
FIG. 5 is a flowchart illustrating an embodiment of a process useful in using the distributed NDT system for planning, inspecting, analyzing, reporting, and sharing of data, such as inspection data.

FIG. 5 is a flowchart of an embodiment of a process 150 suitable for planning, inspecting, analyzing, and/or sharing a variety of data by using the aforementioned devices 12, 14, 16, 22, 92, 94, 96, and the cloud 24. Indeed, the techniques described herein may use the devices 12, 14, 16, 22, 92, 94, 96 to enable processes, such as the depicted process 150, to more efficiently support and maintain a variety of equipment. In certain embodiments, the process 150 or portions of the process 150 may be included in non-transitory computer-readable media stored in memory, such as the memory 17, 21, 25, 95, 99, 103 and executable by one or more processors, such as the processors 15, 19, 23, 93, 97, 101.

In one example, the process 150 may plan (block 152) for inspection and maintenance activities. Data acquired by using the devices 12, 14, 16, 22, 42, 44, 46, and others, such as fleet data acquired from a fleet of turbomachinery 18, from equipment users (e.g., aircraft 104 service companies), and/or equipment manufacturers, may be used to plan (block 152) maintenance and inspection activities, more efficient inspection schedules for machinery, flag certain areas for a more detailed inspection, and so on. The process 150 may then enable the use of a single mode or a multi-modal inspection (block 154) of desired facilities and equipment (e.g., turbomachinery 18). As mentioned above, the inspection (block 154) may use any one or more of the NDT inspection devices 12 (e.g., borescope 14, PTZ camera 16, eddy current inspection device 92, ultrasonic flaw detector 94, digital radiography device 96), thus providing with one or more modes of inspection (e.g., visual, ultrasonic, eddy current, x-ray). In the depicted embodiment, the mobile device 22 may be used to remote control the NDT inspection devices 12, to analyze data communicated by the NDT inspection devices 12, to provide for additional functionality not included in the NDT inspection devices 12 as described in more detail herein, to record data from the NDT inspection devices 12, and to guide the inspection (block 154), for example, by using menu-driven inspection (MDI) techniques, among others.

Results of the inspection (block 154), may then be analyzed (block 156), for example, by using the NDT device 12, by transmitting inspection data to the cloud 24, by using the mobile device 22, or a combination thereof. The analysis may include engineering analysis useful in determining remaining life for the facilities and/or equipment, wear and tear, corrosion, erosion, and so forth. The analysis may additionally include operations research (OR) analysis used to provide for more efficient parts replacement schedules, maintenance schedules, equipment utilization schedules, personnel usage schedules, new inspection schedules, and so on. The analysis (block 156) may then be reported (block 158), resulting in one or more reports 159, including reports created in or by using the cloud 24, detailing the inspection and analysis performed and results obtained. The reports 159 may then be shared (block 160), for example, by using the cloud 24, the mobile device 22, and other techniques, such as workflow sharing techniques. In one embodiment, the process 150 may be iterative, thus, the process 150 may iterate back to planning (block 152) after the sharing (block 160) of the reports 159. By providing for embodiments useful in using the devices (e.g., 12, 14, 16, 22, 92, 94, 96) described herein to plan, inspect, analyze, report, and share data, the techniques described herein may enable a more efficient inspection and maintenance of the facilities 20, 106 and the equipment 18, 104. Indeed, the transfer of multiple categories of data may be provided, as described in more detail below with respect to FIG. 6.

Figure 6:
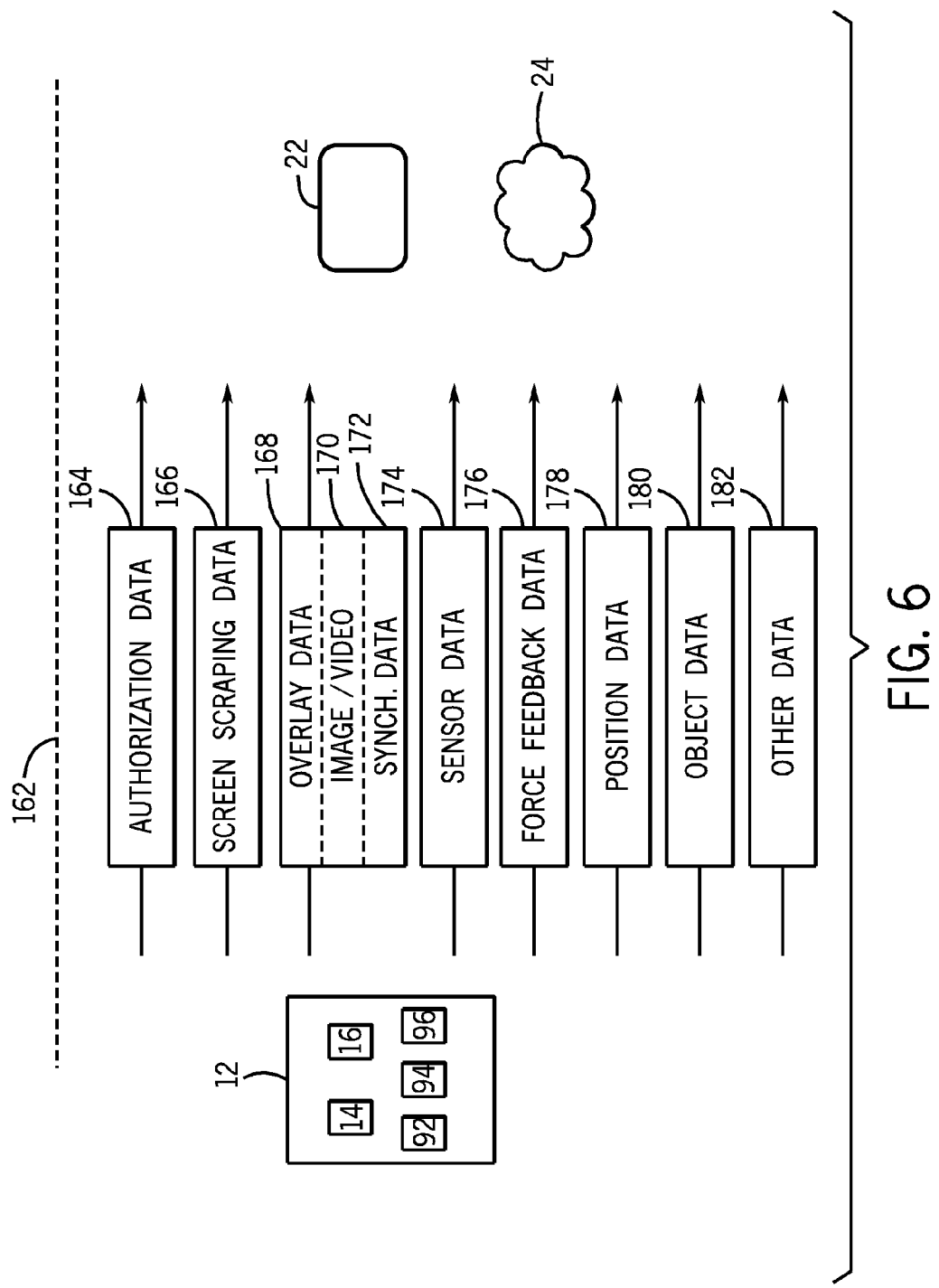
FIG. 6 is a block diagram of an embodiment of information flow through a wireless conduit.

FIG. 6 is a data flow diagram depicting an embodiment of the flow of various data categories originating from the NDT inspection devices 12 (e.g., devices 14, 16, 92, 94, 96) and transmitted to the mobile device 22 and/or the cloud 24. As mentioned above, the NDT inspection devices 12 may use a wireless conduit 162 to transmit the data. In one embodiment, the wireless conduit 112 may include WiFi (e.g., 802.11X), cellular conduits (e.g., HSPA, HSPA+, LTE, WiMax), NFC, Bluetooth, PANs, and the like. The wireless conduit 162 may use a variety of communication protocols, such as TCP/IP, UDP, SCTP, socket layers, and so on. In certain embodiments, the wireless conduit 162 may include secure layers, such as SSL, VPN layers, encrypted layers, challenge key authentication layers, token authentication layers, and so on. Accordingly, an authorization data 164 may be used to provide any number of authorization or login information suitable to pair or otherwise authenticate the NDT inspection device 12 to the mobile device 22 and/or the cloud 24. Additionally, the wireless conduit 162 may dynamically compress data, depending on, for example, currently available bandwidth and latency. The mobile device 22 may then uncompress and display the data. Compression/decompression techniques may include H.261, H.263, H.264, moving picture experts group (MPEG), MPEG-1, MPEG-2, MPEG-3, MPEG-4, DivX, and so on.

In certain modalities (e.g., visual modalities), images and video may be communicated by using certain of the NDT inspection devices 12. Other modalities may also send video, sensor data, and so on, related to or included in their respective screens. The NDT inspection device 12 may, in addition to capturing images, overlay certain data onto the image, resulting in a more informative view. For example, a borescope tip map may be overlaid on the video, showing an approximation of the disposition of a borescope tip during insertion so as to guide the operator 26 to more accurately position the borescope camera 126. The overlay tip map may include a grid having four quadrants, and the tip 136 disposition may be displayed as dot in any portion or position inside of the four quadrants. A variety of overlays may be provided, as described in more detail below, including measurement overlays, menu overlays, annotation overlays, and object identification overlays. The image and video data, such as the video 84, may then be displayed, with the overlays generally displayed on top of the image and video data.

In one embodiment, the overlays, image, and video data may be "screen scraped" from the screen 135 and communicated as screen scrapping data 166. The screen scrapping data 166 may then be displayed on the mobile device 22 and other display devices communicatively coupled to the cloud 24. Advantageously, the screen scrapping data 166 may be more easily displayed. Indeed, because pixels may include both the image or video and overlays in the same frame, the mobile device 22 may simply display the aforementioned pixels. However, providing the screen scraping data may merge both the images with the overlays, and it may be beneficial to separate the two (or more) data streams. For example, the separate data streams (e.g., image or video stream, overlay stream) may be transmitted approximately simultaneously, thus providing for faster data communications. Additionally, the data streams may be analyzed separately, thus improving data inspection and analysis.

Accordingly, in one embodiment, the image data and overlays may be separated into two or more data streams 168 and 170. The data stream 168 may include only overlays, while the data stream 170 may include images or video. In one embodiment, the images or video 170 may be synchronized with the overlays 168 by using a synchronization signal 172. For example, the synchronization signal may include timing data suitable to match a frame of the data stream 170 with one or more data items included in the overlay stream 168. In yet another embodiment, no synchronization data 172 data may be used. Instead, each frame or image 170 may include a unique ID, and this unique ID may be matched to one or more of the overlay data 168 and used to display the overlay data 168 and the image data 170 together.

The overlay data 168 may include a tip map overlay. For example, a grid having four squares (e.g., quadrant grid) may be displayed, along with a dot or circle representing a tip 136 position. This tip map may thus represent how the tip 136 is being inserted inside of an object. A first quadrant (top right) may represent the tip 136 being inserted into a top right corner looking down axially into the object, a second quadrant (top left) may represent the tip 136 being inserted into a left right corner looking down axially, a third quadrant (bottom left) may represent the tip 136 being inserted into a bottom left corner, and a fourth quadrant (bottom right) may represent the tip 136 being inserted into a bottom right corner. Accordingly, the borescope operator 26 may more easily guide insertion of the tip 136.

The overlay data 168 may also include measurement overlays. For example, measurement such as length, point to line, depth, area, multi-segment line, distance, skew, and circle gauge may be provided by enabling the user to overlay one or more cursor crosses (e.g., "+") on top of an image. In one embodiment a stereo probe measurement tip 136, or a shadow probe measurement tip 136 may be provided, suitable for measurements inside of objects, including stereoscopic measurements and/or by projecting a shadow onto an object. By placing a plurality of cursor icons (e.g., cursor crosses) over an image, the measurements may be derived using stereoscopic techniques. For example, placing two cursors icons may provide for a linear point-to-point measurement (e.g., length). Placing three cursor icons may provide for a perpendicular distance from a point to a line (e.g., point to line). Placing four cursor icons may provide for a perpendicular distance between a surface (derived by using three cursors) and a point (the fourth cursor) above or below the surface (e.g., depth). Placing three or more cursors around a feature or defect may then give an approximate area of the surface contained inside the cursors. Placing three or more cursors may also enable a length of a multi-segment line following each cursor.

Likewise, by projecting a shadow, the measurements may be derived based on illumination and resulting shadows. Accordingly, by positioning the shadow across the measurement area, then placing two cursors as close as possible to the shadow at furthermost points of a desired measurement may result in the derivation of the distance between the points. Placing the shadow across the measurement area, and then placing cursors at edges (e.g., illuminated edges) of the desired measurement area approximately to the center of a horizontal shadow may result in a skew measurement, otherwise defined as a linear (point-to-point) measurement on a surface that is not perpendicular to the probe 14 view. This may be useful when a vertical shadow is not obtainable.

Similarly, positioning a shadow across the measurement area, and then placing one cursor on a raised surface and a second cursor on a recessed surface may result in the derivation of depth, or a distance between a surface and a point above or below the surface. Positioning the shadow near the measurement area, and then placing a circle (e.g., circle cursor of user selectable diameter, also referred to as circle gauge) close to the shadow and over a defect may then derive the approximate diameter, circumference, and/or area of the defect.

Overlay data 168 may also include annotation data. For example, text and graphics (e.g. arrow pointers, crosses, geometric shapes) may be overlaid on top of an image to annotate certain features, such as "surface crack." Additionally, audio may be captured by the NDT inspection device 12, and provided as an audio overlay. For example, a voice annotation, sounds of the equipment undergoing inspection, and so on, may be overlaid on an image or video as audio. The overlay data 168 received by the mobile device 22 and/or cloud 24 may then be rendered by a variety of techniques. For example, HTML5 or other markup languages may be used to display the overlay data 168. In one embodiment, the mobile device 22 and/or cloud 24 may provide for a first user interface different from a second user interface provided by the NDT device 12. Accordingly, the overlay data 168 may be simplified and only send basic information. For example, in the case of the tip map, the overlay data 168 may simply include X and Y data correlative to the location of the tip, and the first user interface may then use the X and Y data to visually display the tip on a grid.

Additionally sensor data 174 may be communicated. For example, data from the sensors 126, 140, and x-ray sensor data, eddy current sensor data, and the like may be communicated. In certain embodiments, the sensor data 174 may be synchronized with the overlay data 168, for example, overlay tip maps may be displayed alongside with temperature information, pressure information, flow information, clearance, and so on. Likewise, the sensor data 174 may be displayed alongside the image or video data 170.

In certain embodiments, force feedback or haptic feedback data 176 may be communicated. The force feedback data 176 may include, for example, data related to the borescope 14 tip 136 abutting or contacting against a structure, vibrations felt by the tip 136 or vibration sensors 126, force related to flows, temperatures, clearances, pressures, and the like. The mobile device 22 may include, for example, a tactile layer having fluid-filled microchannels, which, based on the force feedback data 176, may alter fluid pressure and/or redirect fluid in response. Indeed, the techniques describe herein, may provide for responses actuated by the mobile device 22 suitable for representing sensor data 174 and other data in the conduit 162 as tactile forces.

The NDT devices 12 may additionally communicate position data 178. For example, the position data 178 may include locations of the NDT devices 12 in relation to equipment 18, 104, and/or facilities 20, 106. For example, techniques such as indoor GPS, RFID, triangulation (e.g., WiFi triangulation, radio triangulation) may be used to determine the position 178 of the devices 12. Object data 180 may include data related to the object under inspection. For example, the object data 180 may include identifying information (e.g., serial numbers), observations on equipment condition, annotations (textual annotations, voice annotations), and so on. Other types of data 182 may be used, including but not limited to menu-driven inspection data, which when used, provides a set of pre-defined "tags" that can be applied as text annotations and metadata. These tags may include location information (e.g., $1^{st}$ stage HP compressor) or indications (e.g., foreign object damage) related to the object undergoing inspection. Other data 182 may additionally include remote file system data, in which the mobile device 22 may view and manipulate files and file constructs (e.g., folders, subfolders) of data located in the memory 25 of the NDT inspection device 12. Accordingly, files may be transferred to the mobile device 22 and cloud 24, edited and transferred back into the memory 25. By communicating the data 164-182 to the mobile device 22 and the cloud 24, the techniques described herein may enable a faster and more efficient process 150.

Auto-Configuration Based on Object to be Inspected

Figure 7:
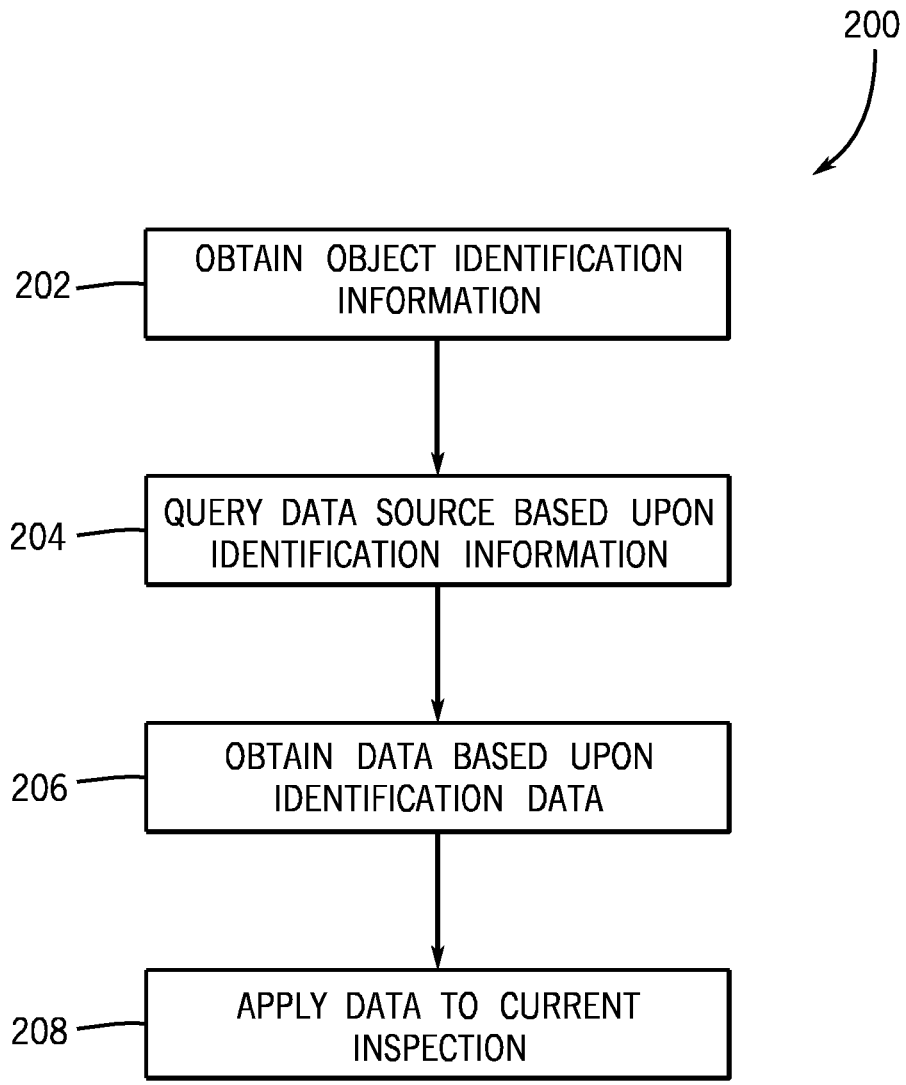
FIG. 7 is a flowchart depicting a process for applying configuration to an inspection instrument based at least in part upon an identity of the object being inspected.

As previously discussed, it may be beneficial to prepare or automatically reconfigure an inspection instrument based upon the object that is to be inspected. This may, for example, increase inspection efficiency, by reducing the workload of an inspector. FIG. 7 is a flowchart depicting a process 200 for applying configuration to an inspection instrument based at least in part upon an identity of the object being inspected. The process 200 may be implemented as executable non-transitory computer instructions stored in a computer readable medium, such as the memories 17, 21, 25, 95, 103 and/or the cloud 24 and may be implemented at inspection time in the field and/or pre-inspection. The process 200 begins with obtaining identification information for the object that will be inspected (block 202). For example, as will be discussed in more detail below, the object may be identified by one of many different methods, such as scanning a barcode, reading a radio frequency identification (RFID) transmitter, computer vision techniques (e.g., visual object recognition [VOR]) or obtaining a user input identifying the object. The inspection instrument may query one or more data sources for data, based at least in part upon the identification information (block 704). The data source(s) may return data relating to the inspection object, which is received by the inspection instrument (block 206). Upon receipt of the data, the inspection instrument applies the data in preparation of the inspection (block 208). For example, the inspection instrument may receive applications, reference materials, historical inspection data, etc. In some embodiments, the applications may include a computer-executable representation of inspection steps for a particular inspection. The applications may include post processing instructions (e.g., instructions to send data to a remote expert for further review, etc.). By implementing the process 200, the inspection instrument may be prepared for inspection without manual interaction, reducing the workload of the inspector. Further, by automatically preparing these devices, errors due to the "human element" may be reduced.

Figure 8:
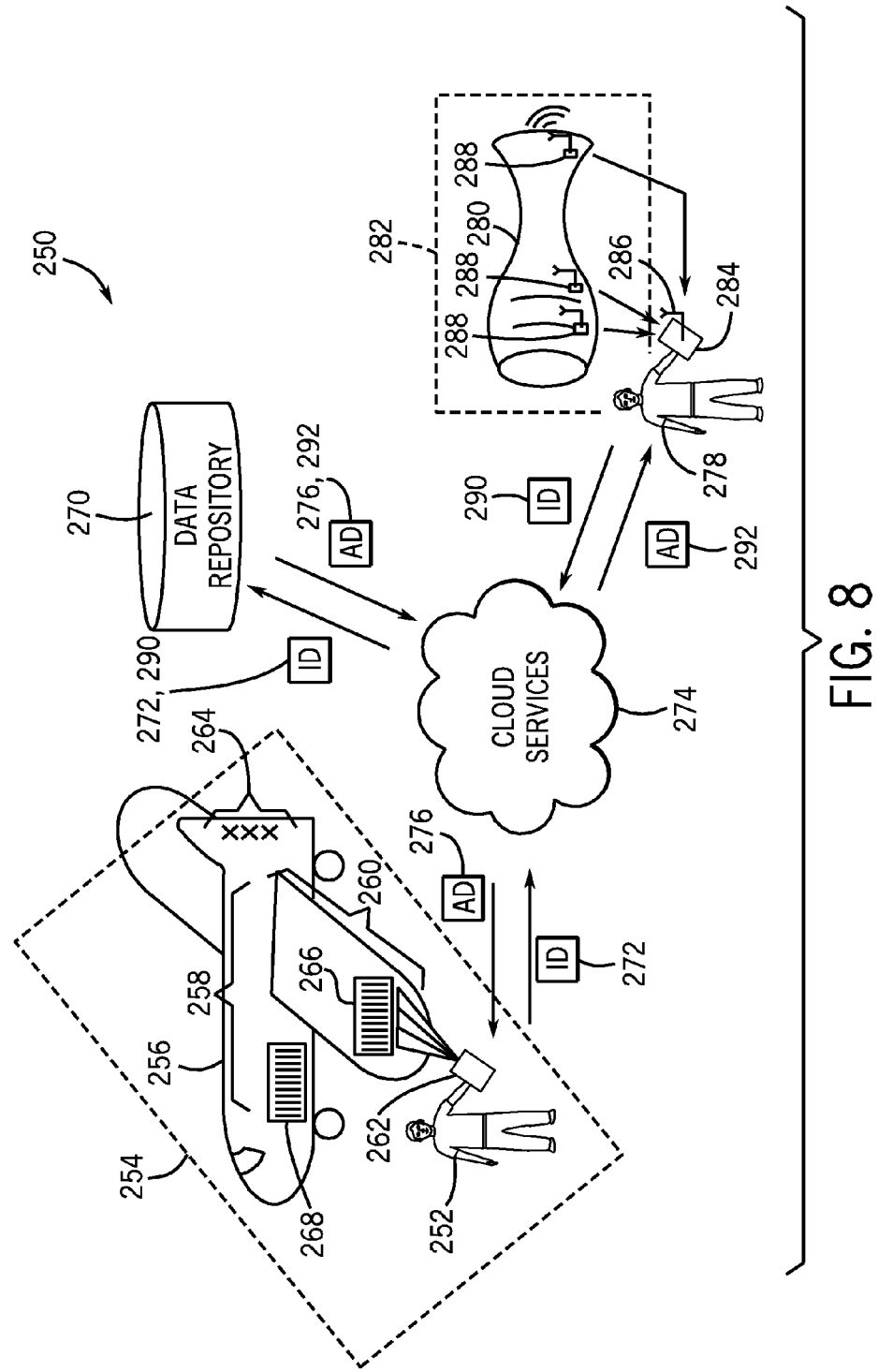
FIG. 8 is a schematic drawing of an inspection system with a plurality of inspection instruments that are enabled to automatically configure themselves based upon an identity of an object being inspected, in accordance with an embodiment.

FIG. 8 is a schematic drawing of an inspection system 250 with a plurality of inspection instruments that are enabled to use the process 200 of FIG. 7 to automatically prepare and configure themselves based upon an identity of an object being inspected, in accordance with an embodiment. In the provided illustration, an inspector 252 enters an inspection site 254. In the current illustration the inspector 252 is tasked with inspecting various portions of an airplane 256. For example, the inspector 252 may be tasked with inspecting a fuselage 258 and the left wing 260. To prepare the inspection instrument 262, the inspector 252 may obtain the identification information (according to block 202 of FIG. 7) of the airplane 256 and/or the specific portion of the airplane 256 that the inspector is going to inspect next. In one embodiment, to obtain the identification information of the airplane, the inspector 252 may obtain an identifying code (e.g., the airplane tail number 264) by capturing an image using a camera of the inspection instrument 262 or by manually inputting the identifying code into the inspection instrument 262. Further, as illustrated in the current figure, the inspector 252 may capture data identifying the left wing 260 through obtaining identifying information at the left wing 260 (e.g., a barcode 266, RFID transmission, etc.). Upon moving to the next inspection point, the inspector could scan identification information located at the fuselage 258, such as the barcode 268.

As discussed above with regards to block 204 of FIG. 7, the inspection instrument 262 may query a data repository 270 (e.g., via cloud-computing services 274 included in the cloud 24). To do this, the inspection instrument 262 may send the identification information 272 to the cloud services 274, where an identity based query is made on the data repository 270. Applicable data 276 is returned from the data repository 270 to the inspection instrument 262. Once the inspection instrument has obtained the applicable data 276, the inspection instrument 262 may automatically apply the data 276 to itself, thus preparing the inspection instrument 262 for inspection of the left wing 210.

Multiple inspectors may make use of the cloud services 274 and the data repository 270 at the same time. For example, in the illustrated example, an inspector 278 is tasked with inspecting a gas turbine 280 at inspection site 282 at the same time inspector 252 is inspecting the airplane 206. The inspector 278 has an inspection instrument 284 equipped with an RFID receiver 286. RFIDs 288 are placed at various portions of the turbine F280, providing identification information as to a particular inspection point. The RFID receiver 286 may use near-field communications to obtain the identification information 290 for a particular portion from the RFIDs 288. The identification information 290 is sent through the cloud services 274 to the data repository 270, where applicable data 292 is transmitted back to the inspection instrument 284. Based upon this data 292, the inspection instrument 284 may prepare and configure itself for inspection. In other embodiments, the inspectors 252, 278 may be guided to desired locations (e.g., inspection points) by using techniques such as indoor GPS, triangulation (e.g., WiFi triangulation, radio triangulation), and the like.

Figure 9:
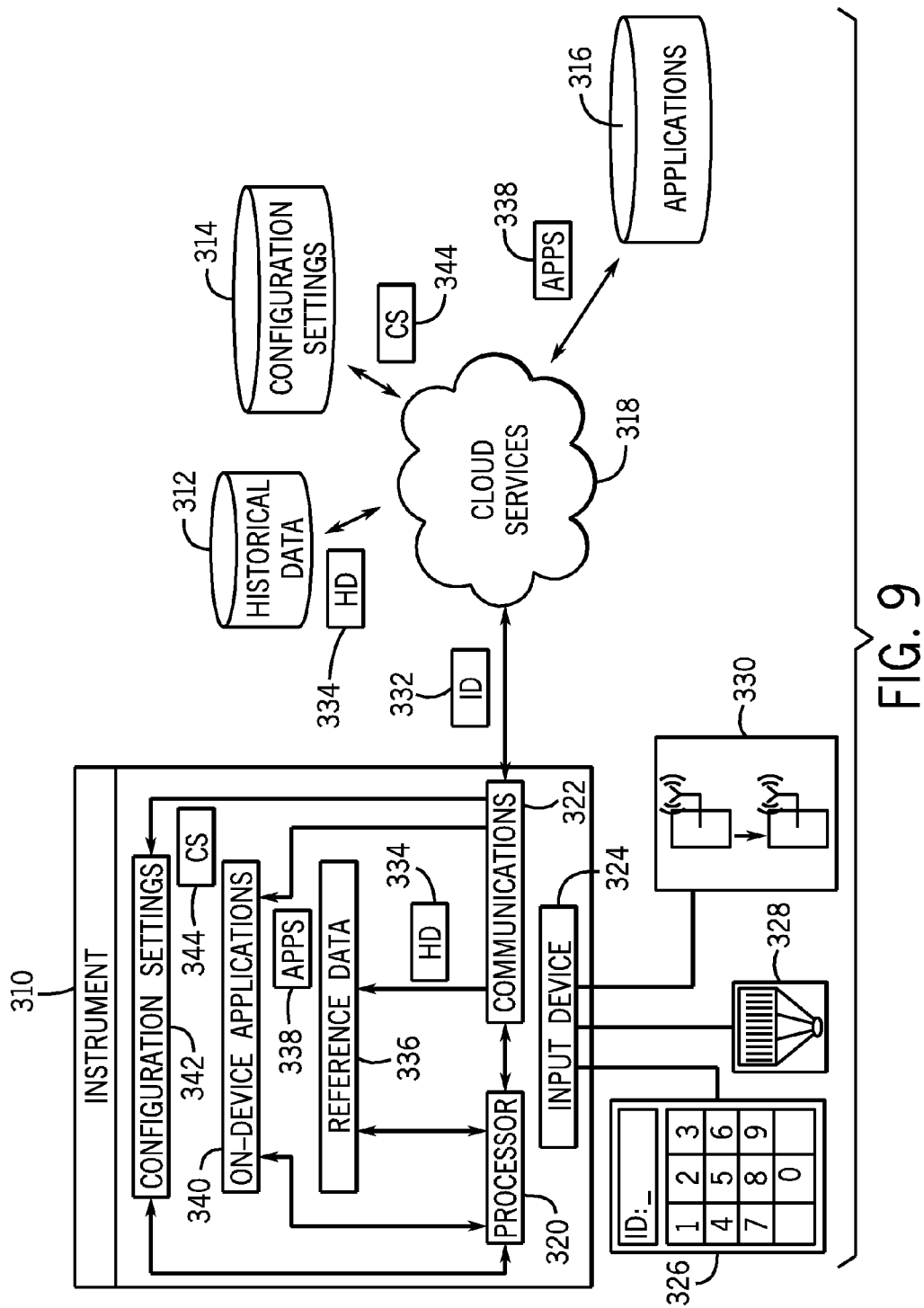
FIG. 9 is a schematic drawing of the inspection instrument of FIG. 8 accessing a plurality of data sources for automatic configuration, in accordance with an embodiment.

FIG. 9 is a schematic drawing of an inspection instrument 310 (e.g., the inspection instrument 262 or 284 of FIG. 8) equipped to access a plurality of data sources (e.g., historical data repository 312, configuration settings repository 314, and applications repository 316, or other data provider, such as an automated application builder, which may create an application in an automated fashion based on the object identifier and specifications relating to the object identifier) via cloud services 318, such that the inspection instrument 310 may automatically prepare and configure itself, in accordance with an embodiment.

To prepare and configure itself, the inspection instrument 310 may gather reference data relating to the planned inspection. For example, the historical data repository 312 may contain historical data relating to previous inspections of a particular object. This information may be useful to the inspector (e.g., to send inspection trends, etc.). Additionally, the inspection instrument 310 may configure itself, using configuration settings provided by the configuration settings repository 314. For example, a borescope may automatically fine tune settings for lighting, positioning, storage locations, tip configurations, etc., based upon data provided in the configuration settings repository 314 and/or any other data repository. Further, the inspection instrument (e.g., NDT devices 12) may automatically download applications 316, such as menu driven instruction (MDI) applications or digitized usage manual applications from an applications repository 316. Accordingly, the inspections may include up-to-date configurations settings, inspection procedures, instructions, and the like.

To achieve these functions, the inspection instrument 310 (e.g., NDT inspection device 12) may include a processor 320 and communications circuitry 322. The communications circuitry 322 may make use of any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless LAN (Wi-Fi) (e.g., IEEE 802.11a, IEEE 802.11b, IEEE 802.11g and/or IEEE 802.11n), Wi-MAX, and/or Short Message Service (SMS), or any other suitable communication protocol, including communication protocols not yet developed as of the filing date of this document. Further, the inspection instrument may have an input device 324 to capture the identification information. In certain embodiments, the input device 324 may include a manual user input, such as a microphone or a keypad 326. The input device 324 could alternatively include a barcode scanner 328 or an RFID reader 330, a GPS receiver, a radio receiver, or a combination thereof.

The communications circuitry 322 may send the identification information 332 obtained by the input device 324 to the various repositories 312, 314, and 316, to receive data relating to the identification information 332. Historical data 334 relating to the inspection information 332 may be provided to a reference data store 336 on the inspection instrument 310. Further, the communications circuitry 322 may receive a reference (e.g., download link or pointer) to applications 338 or may receive the applications 338 themselves. These applications 338 may aid in completion of the inspection and may be downloaded to an application data store 340 of the inspection instrument 310. Configuration settings 342 of the instrument 310 may be updated, via the processor 320, using configuration settings 344 provided from the configuration settings repository 314 and/or any other data repository. Accordingly, by providing the identification information 332, the inspection instrument 310 may automatically pull and display reference data (e.g., historical data 334, may automatically download inspection applications 338 and apply configuration settings 344, or any combination of one or more of these.

Figure 10:
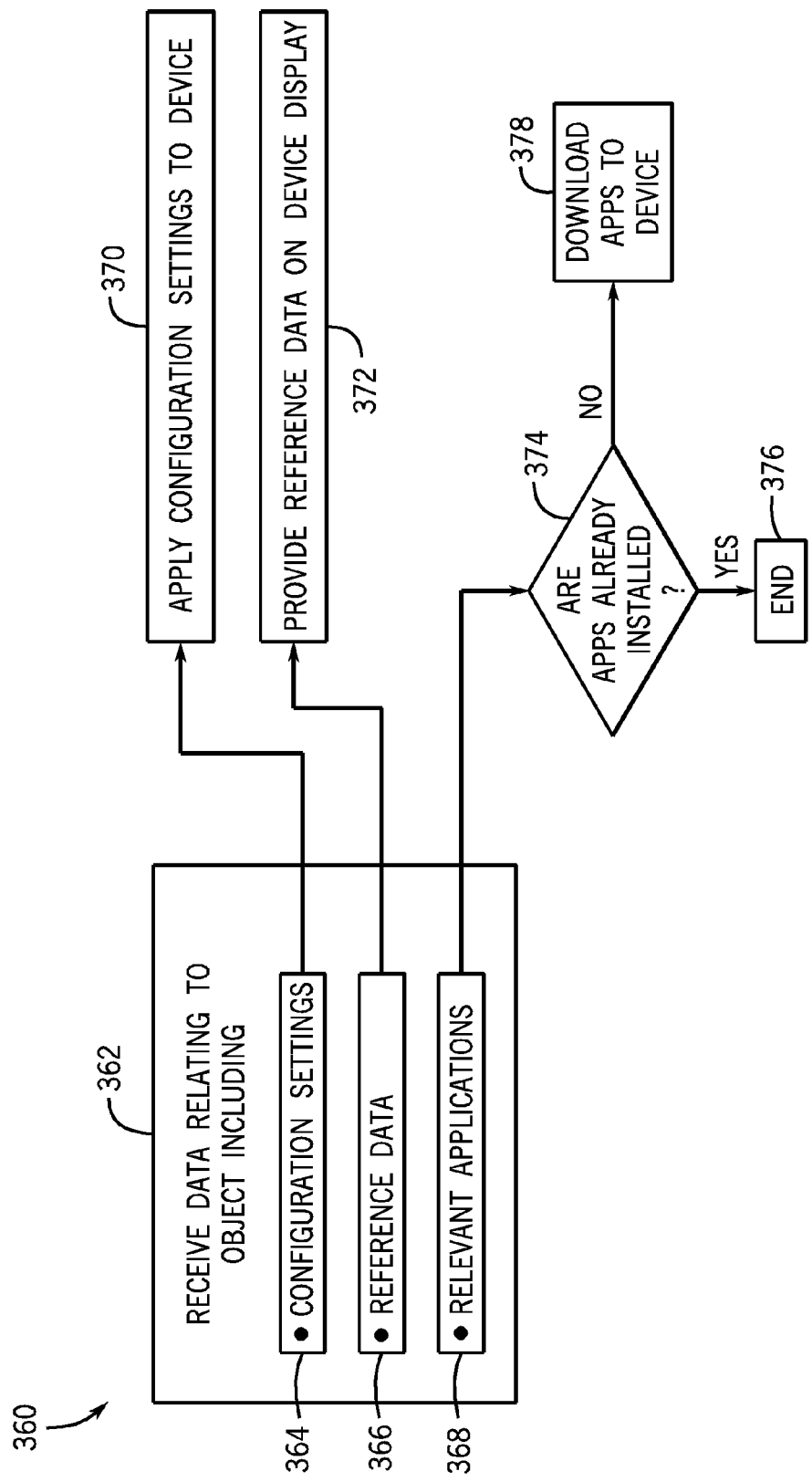
FIG. 10 is a flowchart depicting a more detailed process for applying the configuration data of FIG. 7 to the inspection instrument, in accordance with an embodiment.

FIG. 10 is a flow chart depicting a more detailed process 360 for applying the configuration data of FIG. 7 to the inspection instrument, in accordance with an embodiment. First, the data is received (block 362). The data may include configuration settings 364, reference data 366, relevant applications 368, such as workflow applications that provide workflow steps, configuration details, and/or reference materials for one or more of the workflow steps, and/or other useful information. Additionally, historical inspection data may also be provided. Upon receiving configuration settings 364, reference data 366, relevant applications 368, historical inspection data, and/or other useful information, the instrument may apply the configuration settings to itself (block 370). In some embodiments, it may be beneficial to request inspector approval before applying the configuration changes. In such embodiments, the configuration changes may only occur upon explicit allowance by the inspector. Alternatively, in some embodiments, the configuration changes may automatically occur without any prompting of the inspector.

Upon receiving reference data (e.g., data that may be useful during the inspection process, such as, but not limited to, data from prior inspections, references manuals, service bulletins, or training and instructional materials), the reference data may be provided to the inspector, for example, by displaying relevant information on a display of the inspection instrument (block 372). When a number of inspections have been performed, there may be quite a bit of relevant prior inspection data. Accordingly, the inspector may specify a particular time frame for reference data that should be provided by the inspection instrument. For example, the inspector could specify that only reference data obtained in the last year be provided by the inspection instrument.

In some instance, the reference data may be quite complex. Accordingly, the processing power or other resource usage may be quite large. Thus, a server or other data provider service may provide pre-processing of the reference data prior to providing the reference data to the inspection instrument. For example, if an inspector were inspecting an engine, the reference data may include a 3D reference model. However, the resource usage for rendering the 3D model may be quite significant. By enabling a server and/or other data service provider to render or initialize the 3D model, additional processing may be possible, resulting in a more efficient use of inspection system resources.

When a listing of relevant applications for the inspection is provided, the applications may be downloaded to the inspection instrument. For example, a determination 374 may be made as to whether the application is already installed on the inspection instrument. If the application is already installed, no action is taken 376. If the application is not installed, the application is downloaded and installed to the inspection instrument (block 378).

In addition to applying configuration data to an inspection instrument, the presently disclosed techniques may also provide a process in which scanning technology such as optical character recognition (OCR) technology, barcode scanning technology, radio frequency identification (RFID) technology, computer vision techniques (e.g., visual object recognition [VOR]), near-field communication technology, a digital camera, scanner, sensor, and the like may be used to assist the inspector 250 (or 278, etc.) in generating a report summarizing the results of an inspection process or of various objects in the NDT system 10 being inspected, generating an inspection template for the inspection process of an area or various objects in the NDT system 10, capturing metadata for data associated with the inspection process with various objects in the NDT system 10, entering data related to an inspection process for various objects in the NDT system 10, and the like. By using these scanning technologies, the inspector 250 may perform the above mentioned tasks without manually entering the data using a user interface such as a keyboard, a keypad, or the like. That is, an application being executed by the mobile device 22, the NDT inspection device 12, or the like may engage some scanning technology that may be present on the mobile device 22 or the NDT inspection device 12 to assist the inspector 250 in performing his inspection tasks.

For instance, the application may use OCR (optical character recognition) technology or the like to create a report based on the scanned data. The application may also use OCR technology or the like to scan an existing worksheet or inspection report to generate an inspection template that may be used by the inspector 250 or the like to enter data during the inspection process. The existing worksheet or inspection report may include a serial number for an asset being inspected using the NDT inspection device 12, a number of engine hours for the asset, a mode of the asset, and the like. The application may then recognize data entries such as the serial number, the number of engine hours, or the like in the scanned document and may enter these entries into a report that may be currently being populated by the inspector 250 during his inspection process, into an inspection template associated with the inspection process, into metadata for objects being inspected or the inspection process, or the like. These and other embodiments in which the scanning technology may be used in conjunction with the inspection process using NDT inspection devices 12 are described in greater detail below with reference to FIGS. 11-13.

Figure 11:
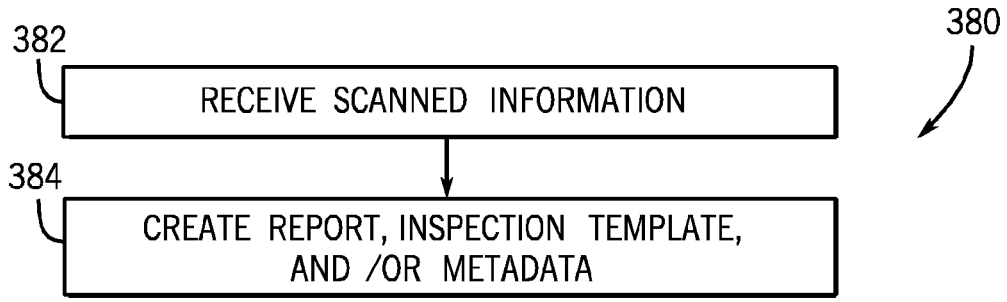
FIG. 11 is a flowchart depicting a process for generating a report, an inspection template, or metadata using information in the NDT system of FIG. 1, in accordance with an embodiment.

Referring now to FIG. 11, FIG. 11 illustrates an embodiment of a process 380 for creating a report, an inspection template, metadata or the like that may be associated with an inspection process for the NDT system 10 using scanning technology. In certain embodiments, the process 380 or portions of the process 380 may be included in non-transitory computer-readable media stored in memory, such as the memory 15, 19, 23, 25, 93, 97, 101 and executable by one or more processors, such as the processors 17, 21, 25, 95, 99, 103 and the cloud 24.

In one embodiment, an application containing computer instructions executable by the mobile device 22, the NDT inspection devices 12, and/or the cloud 24 may be used in conjunction with the certain scanning technology to collect data or information that may be related to the inspection of a piece of equipment (e.g., devices 12, 14, 16, 22, 42, 44, 46) within the NDT system 10, an inspection process associated with the NDT system 10, or the like. The collected data may then be used to generate reports 159 related to the inspection of the NDT system 10, generate an inspection template related to the inspection of the NDT system 10, generate metadata related to the inspection of the NDT system 10, or the like. Although the process 380 depicts a particular order in which the process 380 may be performed, it should be noted that the process 380 may also be performed in a different order.

Keeping the foregoing in mind, the application may first receive information (block 382) that may have been scanned by the scanning technology described above. The scanned information may include identification information for object and/or assets in the NDT system 10, information related to the inspection process for the NDT system, information related to the NDT system 10 or components in the NDT system 10, or any text that may be present in the NDT system 10. For example, the scanned information may include information located on a nameplate attached to an asset in the NDT system 10, a worksheet related to an item in the NDT system 10, a specification document related to an item in the NDT system 10, or any other item in the NDT system 10 that may have text characters that may be scanned.

The scanned information may be acquired using at least one of the scanning technologies described above that may be disposed on the mobile device 22, the NDT inspection device 12, or the like. In one embodiment, the scanned information may be determined by applying OCR technology on an image or video acquired using a digital camera or the like. Additionally or alternatively, the scanned information may be acquired as the inspector 250 scans various texts located in the NDT system 10 using a video probe or another type of scanning technology. For instance, the inspector 250 may use a video probe, included, for example, in the borescope 14, to scan text depicted on a nameplate for an asset in the NDT system 10. The scanned text may include a title field and a corresponding data field. As such, the scanned information may include the title of the entry on the nameplate (e.g., part number) and a corresponding data entry (e.g., a numerical value that indicates the part number).

After receiving the scanned information, the application may create a report, an inspection template, metadata, or the like (block 384) based on the received scanned information. By way of example, the application may generate the report or the inspection template based on the scanned information. As such, the application may identify the title fields, the data fields, and other information in the scanned information and generate the report or the inspection template such that they may be populated with the title fields and the data fields.

In one embodiment, the scanned information may correspond to an existing (i.e., physical) inspection report that may be populated by the inspector 250 during his inspection. As such, the application may receive (at block 382) data that corresponds to a scanned version of the inspection report. The application may then create a digital version of the inspection report that may be populated by the inspector 250 via the mobile device 22, the NDT inspection device 12, or the like. In certain embodiments, after scanning the existing inspection report, the application may identify fields that may involve data entry or the like. The application may then use these identified fields to generate fields for a report or report template that may be used in the inspection process.

By way of example, the scanned information may correspond to a manual that describes a process for inspecting a specific asset that may be part of the NDT system 10, a component on the asset, an area associated with the NDT system 10, or the like. In this example, the application may analyze and parse the described process to create an inspection template or guide for the inspector 250 to follow while performing an inspection.

As mentioned above, the application may also generate metadata based on the scanned data. For example, the application may first receive identification information associated with an asset being inspected. The application may store the identification data as data in a memory. The application may then receive additional information using the scanning technology such as a manufactured date, a last inspection date, different part numbers, and the like. Here, the application may generate metadata that includes the additional scanned information and associate the metadata with the corresponding stored data.

In one example, the scanned information may include revision or form information related to a scanned worksheet. That is, the scanned worksheet may include a revision number or revision date that may indicate when the scanned information was last revised. In this case, the application may recognize the revision information from the scanned worksheet and generate metadata that may be associated with an inspection template, which may be created based on the scanned worksheet. As such, the metadata may indicate revision information that may correspond to the revision date of the worksheet.

Figure 12:
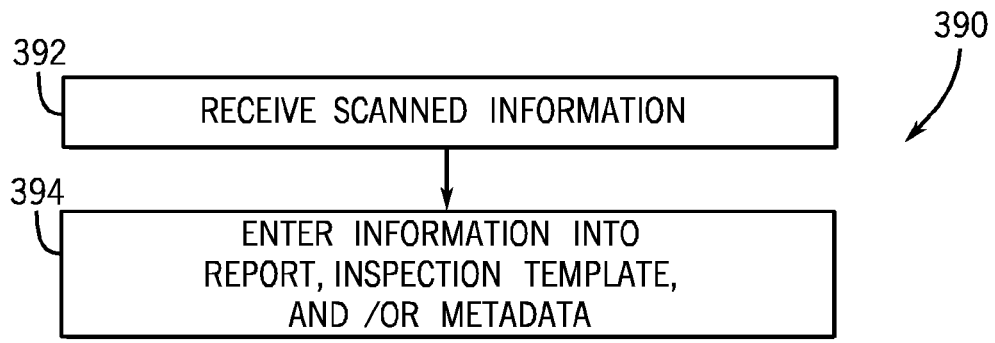
FIG. 12 is a flowchart depicting a process for entering data into a report, inspection template, or metadata that corresponds to the NDT system of FIG. 1, in accordance with an embodiment.

In addition to generating reports, inspection templates, and metadata, the application may enter data into an existing report, inspection template, or metadata using the scanning technology described above. FIG. 12 illustrates an embodiment of a process 390 for entering data into a report, inspection template, or metadata that may be used during an inspection process that corresponds to the NDT system 10 using scanning technology. In certain embodiments, the process 390 or portions of the process 390 may be included in non-transitory computer-readable media stored in memory, such as the memory 15, 19, 23, 25, 93, 97, 101 and executable by one or more processors, such as the processors 17, 21, 25, 95, 99, 103 and the cloud 24.

In one embodiment, an application containing computer instructions executable by the mobile device 22, the NDT inspection devices 12, and/or the cloud 24 may be used in conjunction with the scanning technology described above to enter data that may be related to the inspection of a piece of equipment (e.g., devices 12, 14, 16, 22, 42, 44, 46) within the NDT system 10 into a report. Although the process 390 depicts a particular order in which the process 390 may be performed, it should be noted that the process 390 may also be performed in a different order.

Referring now to FIG. 12, the application may receive scanned information (block 392), as described above with reference to block 382 of FIG. 11. After receiving the scanned information, the application may enter the scanned information into an existing report, inspection template, metadata, or the like (block 394). That is, the scanned information may be used to populate or enter information into a field in a report, inspection template, metadata or the like that may be stored in a memory. For example, the inspection template may include a field that may correspond to a serial number for the asset being inspected. Here, the inspector 250 may use a video probe or the like to scan the serial number that may be depicted on a nameplate attached to the asset being inspected. In one embodiment, once the application receives the scanned serial number, the application may identify a field in the inspection template that may be appropriate for the scanned serial number. In another embodiment, the application may receive an input or indication from the inspector 250 that may indicate the appropriate field to enter the scanned serial number. The input or indication may include a touch input on the appropriate field in the report that may be displayed on a screen of the mobile device 22, the NDT inspection device 12, or the like.

As mentioned above, the scanned information may also include metadata that may correspond to a respective field in the inspection report. As such, as the application receives the scanned information, the application may then enter the scanned information into the appropriate field in the inspection report based on the metadata.

The metadata may also indicate a date and/or time in which the scanned information may have been acquired. As such, the application may replace previous data entries in the report or inspection template with recently acquired scanned information based on the data and/or time as indicated in the metadata.

Figure 13:
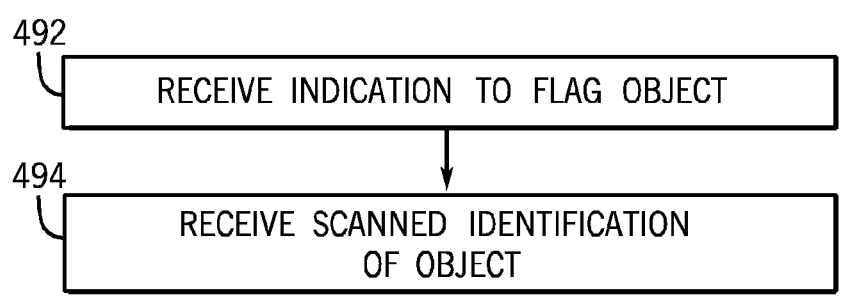
FIG. 13 is a flowchart depicting a process for flagging a report using information in the NDT system of FIG. 1, in accordance with an embodiment.

In addition to entering data in a report, inspection template, metadata, or the like, the application may use the scanning technology to flag assets or any item in the NDT system 10 as non-operating, requesting service, or the like. FIG. 13 illustrates an embodiment of a process 400 for flagging data or an item in the NDT system 10 using scanning technology. In certain embodiments, the process 400 or portions of the process 400 may be included in non-transitory computer-readable media stored in memory, such as the memory 15, 19, 23, 25, 93, 97, 101 and executable by one or more processors, such as the processors 17, 21, 25, 95, 99, 103 and the cloud 24.

In one embodiment, an application containing computer instructions executable by the mobile device 22, the NDT inspection devices 12, and/or the cloud 24 may be used in conjunction with the certain scanning technology to enter data that may be related to the inspection of a piece of equipment (e.g., devices 12, 14, 16, 22, 42, 44, 46) within the NDT system 10 into a report. Although the process 400 depicts a particular order in which the process 400 may be performed, it should be noted that the process 400 may also be performed in a different order.

Referring now to FIG. 13, the application may receive (block 492) an indication to flag an object in the NDT system 10. The object may include any item or asset in the NDT system 10. In one embodiment, the object may include a nameplate or some other text information that may be scanned such that the object may be identified by the corresponding text information. The indication to flag the object may include providing an input such as a key stroke, an input on a graphic or icon displayed on the device executing the application, or the like.

After receiving the indication to flag the object, the application may receive (block 494) scanned information that corresponds to the object being flagged. The application may then designate the object that corresponds to the scanned information as being flagged. In certain embodiments, the application may enable the user to enter a comment to provide some details with regard to the flagging of the object.

Technical effects of the invention include automatically generating reports and entering data into reports, as opposed to manually generating reports or entering data. In this manner, the inspector 250 may more efficiently perform the inspection process.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
obtaining, via a scanning technology associated with a non-destructive testing (NDT) inspection device, a worksheet associated with an inspection of an object being inspected by the NDT inspection device, a specification document associated with the inspection, or any combination thereof; and
generating an inspection template, a report, metadata, or any combination thereof based on the worksheet, the specification document, or any combination thereof.

2. The method of claim 1, wherein the inspection template is associated with the inspection of the object, wherein the report summarizes the inspection, and wherein the metadata is associated with data that corresponds to the inspection.

3. The method of claim 1, wherein the scanning technology comprises optical character recognition (OCR) technology, barcode scanning technology, radio frequency identification (RFID) technology, computer vision techniques (e.g., visual object recognition), near-field communication technology, a digital camera, a scanner, a sensor, or any combination thereof.

4. The method of claim 1, comprising:
obtaining, via the scanning technology, an identification number associated with the object; and
entering the identification number into the inspection template, the report, the metadata, or any combination thereof.

5. The method of claim 1, wherein obtaining the worksheet, the specification document, or any combination thereof comprises:
receiving an image that corresponds to the inspection; and
applying an optical character recognition algorithm to the image.

6. The method of claim 1, wherein the worksheet, the specification document, or any combination thereof is obtained using a video probe.

7. The method of claim 1, wherein generating the inspection template comprises:
receiving scanned information comprising one or more text objects;
identifying one or more title fields, one or more data fields, or any combination thereof from the scanned information; and
generating the inspection template based on the one or more title fields, the one or more data fields, or any combination thereof.

8. A system, comprising:
a non-destructive testing (NDT) inspection device, comprising:
scanning technology configured to obtain:
an image that corresponds to an inspection report for inspecting an object using the NDT inspection device; and
a value regarding an inspection of the object being inspected by the NDT inspection device, and
a processor configured to:
identify one or more data entry fields in the image;
create a digital version of the inspection report having the data entry field;
receive, via the scanning technology, the value; and
enter the value into the one or more data entry fields of the digital version of the inspection report associated with the inspection.

9. The system of claim 8, wherein the processor is configured to enter the value by:
receiving an input indicative of one of the data entry fields; and
entering the value into the one of the data entry fields.

10. The system of claim 8, wherein the processor is configured to enter the value by:
determining one of the data entry fields in the inspection report based on metadata associated with the value; and
entering the value into the one of the data entry fields.

11. The system of claim 8, wherein the processor is configured to enter the information by:
determining whether the value was obtained prior to an existing value present in one of the data entry fields in the inspection report; and
replacing the existing value with the value in the one of the data entry fields when the value was not obtained prior to the existing value.

12. The system of claim 11, wherein the processor is configured to determine whether the value was obtained prior to the existing value based on metadata associated with the value and the existing value.

13. The system of claim 8, wherein the scanning technology comprises a camera, a video probe, a scanner, or any combination thereof.

14. The system of claim 8, wherein the processor is configured to enter the value into the one or more data entry fields by generating metadata having the value wherein the metadata is associated with the inspection report.

15. The system of claim 8, wherein the processor is configured to receive an input configured to flag the object when the value is received.

16. A tangible, non-transitory, computer readable medium, comprising computer readable instructions configured to:
receive an image that corresponds to an inspection report;
receive, via a non-destructive testing (NDT) inspection device, information that corresponds to an inspection; and
generating a report template based on the inspection report and the information by:
identifying one or more data entry fields in the image; and
creating a digital version of the inspection report having the data entry fields.

* * * * *